United States Patent [19]

Vlassara et al.

[11] Patent Number: 5,852,174
[45] Date of Patent: Dec. 22, 1998

[54] ANTIBODIES TO LIVER DERIVED RECEPTORS FOR ADVANCED GLYCOSYLATION ENDPRODUCTS AND USES THEREFOR

[75] Inventors: Helen Vlassara, Shelter Island, N.Y.; Zhi Yang, Menlo Park, Calif.; Anthony Cerami, New York, N.Y.

[73] Assignee: The Rockefeller University, N.Y., N.Y.

[21] Appl. No.: 479,149

[22] Filed: Jun. 7, 1995

Related U.S. Application Data

[60] Division of Ser. No. 749,438, Aug. 23, 1991, Pat. No. 5,585,344, which is a continuation-in-part of Ser. No. 453,958, Dec. 20, 1989, abandoned, which is a division of Ser. No. 91,534, Sep. 3, 1987, Pat. No. 4,900,747, which is a continuation-in-part of Ser. No. 907,747, Sep. 12, 1986, abandoned, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.[6] .............................. C07K 16/28; C12N 5/12
[52] U.S. Cl. .................. 530/387.9; 530/388.22; 530/388.85; 530/389.1; 530/391.1; 530/391.3; 435/332
[58] Field of Search ........................ 530/387.9, 388.22, 530/388.85, 389.1, 391.1, 391.3; 435/332

[56] References Cited

PUBLICATIONS

Yang, Z., et al. J. Exp. Med. 174: p. 515 published on Aug. 23, 1991.
Vlassara, H. et al. Proc. Natl. Acad. Sci. U.S.A. 82:5588 (1985).
Vlassara, H. et al. J. Exp. Med. 160:197 (1984).
Radoff, S. Diabetes 39:1510 (1910).
Radoff, S., et al. Arch Biochem. Biophys. 263:418 (1988).
Esposito, C. et al. J. Exp. Med. 170:1387 (1989).
Skolnïk, E. et al. Diabetes J. Exp. Med. 931:939 (1991).

*Primary Examiner*—Paula K. Nutzell
*Assistant Examiner*—Nancy A. Johnson
*Attorney, Agent, or Firm*—Klauber & Jackson

[57] ABSTRACT

The present invention relates to receptors for advanced glycosylation endproducts derived from rat liver membranes, and that specifically comprise proteins determined to possess molecular masses of about 90 kD and 60 kD, respectively, as assessed by migration during SDS-PAGE. Partial N-terminal sequences have been determined and diagnostic and therapeutic agents, compositions and methods are proposed. Antibodies to the 90 kD and 60 kD receptor proteins are disclosed.

10 Claims, 15 Drawing Sheets

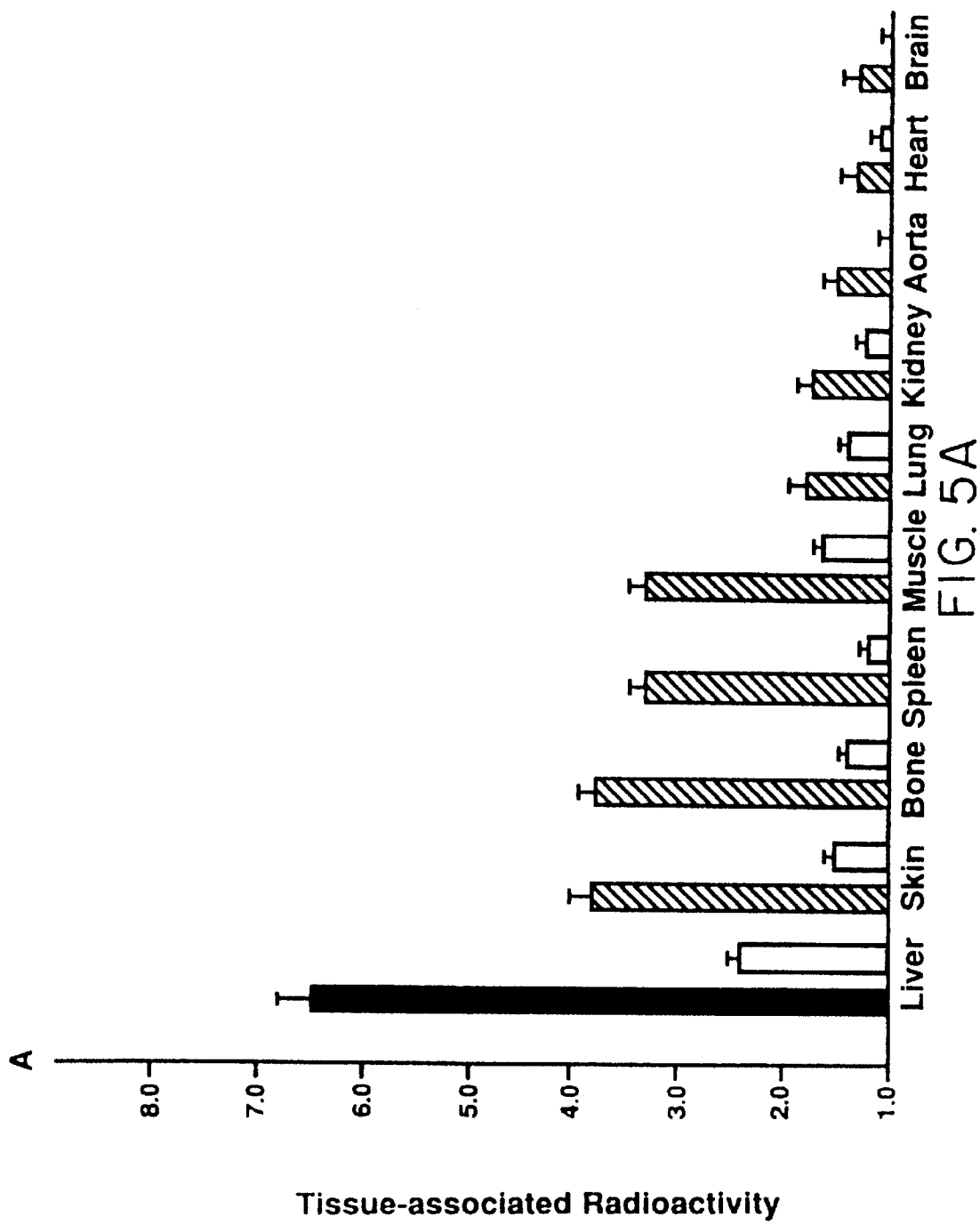

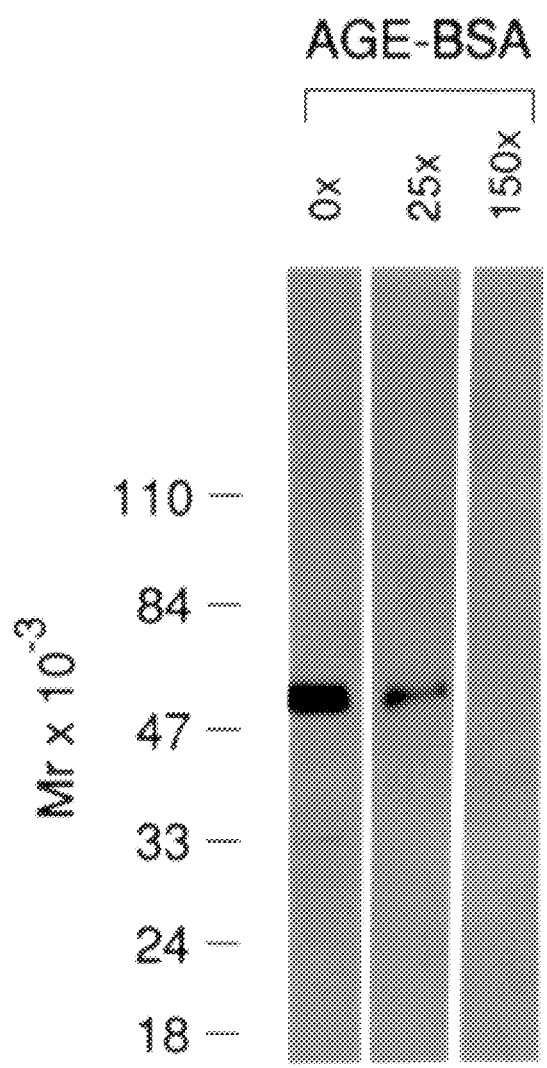

FIG. 11

X Glu Val Lys Leu Pro Asp Met Val Ser Leu X Asp
1　　　　　　　　5　　　　　　　　　10

FIG. 12

X Gly Pro Arg Thr Leu Val Leu Leu Asp Asn Leu Asn Val Arg
1　　　　　　　5　　　　　　　　　10

Arg Asp Thr His X Leu Phe Phe
15　　　　　　　　20

ANTIBODIES TO LIVER DERIVED RECEPTORS FOR ADVANCED GLYCOSYLATION ENDPRODUCTS AND USES THEREFOR

CROSS-REFERENCE TO RELATED APPLICATIONS

This Application is a Division of application Ser. No. 07/749,438 filed Aug. 23, 1991 now U.S. Pat. No. 5,585,344, which is a Continuation-In-Part of application Ser. No. 453,958, filed Dec. 20, 1989 now abandoned, which is in turn, a Division of application Ser. No. 091,534, filed Sep. 3, 1987, now U.S. Pat. No. 4,900,747, issued Feb. 13, 1990, which is in turn, a Continuation-In-Part of application Ser. No. 907,747, filed Sep. 12, 1986, now abandoned; all of the above preceding applications by Helen Vlassara, Michael Brownlee and Anthony Cerami, said Ser. No. 907,747, in turn, a Continuation-In-Part of application Ser. No. 798,032, filed Nov. 14, 1985, by Anthony Cerami, Peter Ulrich and Michael Brownlee, now U.S. Pat. No. 4,758,583, which is, in turn, a Continuation-In-Part of application Ser. No. 590,820, now U.S. Pat. No. 4,665,192, filed Mar. 19, 1984 by Anthony Cerami alone.

This invention was made with partial assistance from grant Nos. AG 8245 and DK 19655 from the National Institutes of Health. The government may have certain rights in this invention.

Priority under 35 U.S.C. §120 is claimed as to all of the above earlier filed Applications, and the disclosures thereof are incorporated herein by reference.

RELATED PUBLICATIONS

The Applicants are co-authors of the following articles directed to the subject matter of the present invention: "FUNCTION OF MACROPHAGE RECEPTOR FOR NONENZYMATICALLY GLYCOSYLATED PROTEINS IS MODULATED BY INSULIN LEVELS", Vlassara, Brownlee and Cerami, DIABETES (1986), Vol. 35 Supp. 1, Page 13a; "ACCUMULATION OF DIABETIC RAT PERIPHERAL NERVE MYELIN BY MACROPHAGES INCREASES WITH THE PRESENCE OF ADVANCED GLYCOSYLATION ENDPRODUCTS", Vlassara, H., Brownlee, M., and Cerami, A. J. EXP. MED. (1984), Vol. 160, pp. 197–207; "RECOGNITION AND UPTAKE OF HUMAN DIABETIC PERIPHERAL NERVE MYELIN BY MACROPHAGES", Vlassara, H., Brownlee, M., and Cerami, A. DIABETES (1985), Vol. 34, No. 6, pp. 553–557; "HIGH-AFFINITY-RECEPTOR-MEDIATED UPTAKE AND DEGRADATION OF GLUCOSE-MODIFIED PROTEINS: A POTENTIAL MECHANISM FOR THE REMOVAL OF SENESCENT MACROMOLECULES", Vlassara H., Brownlee, M., and Cerami, A., PROC. NATL. ACAD. SCI. U.S.A. (September 1985), Vol. 82, pp. 5588–5592; "NOVEL MACROPHAGE RECEPTOR FOR GLUCOSE-MODIFIED PROTEINS IS DISTINCT FROM PREVIOUSLY DESCRIBED SCAVENGER RECEPTORS", Vlassara, H., Brownlee, M., and Cerami, A. JOUR. EXP. MED. (1986), Vol. 164, pp. 1301–1309; "ROLE OF NONENZYMATIC GLYCOSYLATION IN ATHEROGENESIS", Cerami, A., Vlassara, H., and Brownlee, M., JOURNAL OF CELLULAR BIOCHEMISTRY (1986), Vol. 30, pp. 111–120; "CHARACTERIZATION OF A SOLUBILIZED CELL SURFACE BINDING PROTEIN ON MACROPHAGES SPECIFIC FOR PROTEINS MODIFIED NONENZYMATICALLY BY ADVANCED GLYCOSYLATION END PRODUCTS", Radoff, S., Vlassara, H. and Cerami, A., ARCH. BIOCHEM. BIOPHYS (1988), Vol. 263, No. 2, pp. 418–423; "ISOLATION OF A SURFACE BINDING PROTEIN SPECIFIC FOR ADVANCED GLYCOSYLATION ENDPRODUCTS FROM THE MURINE MACROPHAGE-DERIVED CELL LINE RAW 264.7", Radoff, S., Vlassara, H., and Cerami, A., DIABETES, (1990), Vol. 39, pp. 1510–1518; "TWO NOVEL RAT LIVER MEMBRANE PROTEINS THAT BIND ADVANCED GLYCOSYLATION ENDPRODUCTS: RELATIONSHIP TO MACROPHAGE RECEPTOR FOR GLUCOSE-MODIFIED PROTEINS", Yang, Z., Makita, Z., Horii, Y., Brunelle, S., Cerami, A., Sehajpal, P., Suthanthiran, M. and Vlassara, H., J. EXP. MED., (1991), Vol. 174 pp. 515–524. All of the foregoing publications are incorporated herein by reference.

BACKGROUND OF THE INVENTION

The present invention relates generally to the nonenzymatic glycosylation of proteins, and particularly to the discovery of binding partners to advanced glycosylation endproducts such as AGE receptors, that may serve in the diagnosis and treatment of conditions in which the presence or activity of such advanced glycosylation endproducts may be implicated.

Glucose and other reducing sugars attach nonenzymatically to the amino groups of proteins in a concentration-dependent manner. Over time, these initial Amadori adducts undergo further rearrangements, dehydrations and cross-linking with other proteins to accumulate as a family of complex structures which are referred to as Advanced Glycosylation Endproducts (AGEs). Although this chemistry has been studied by food chemists for many years, it was only in the past decade that the presence of AGEs in living tissues has been established. The excessive deposition of these products on structural body proteins as a function of age and elevated glucose concentration, taken together with evidence of effective prevention of tissue pathology by an AGE inhibitor, aminoguanidine, has lent support to the hypothesis that the formation of AGEs plays a role in the long term complications of aging and diabetes.

Since the amount of AGEs found in human tissues is less than could be predicted from protein/glucose incubation studies in vitro, the applicants herein proposed several years ago that there might be normal mechanisms to remove those long-lived proteins which had accumulated AGEs in vivo. Particularly, and as set forth initially in parent application Ser. No. 907,747, now abandoned and the above-referenced applications that have followed, monocytes/macrophages were found to display high affinity surface binding activity specific for AGE moieties, independent of the protein which was AGE-modified. This macrophage AGE-receptor was shown to differ from other known scavenger receptors on these cells. In addition, an endogenous means for the in vivo elimination or removal of advanced glycosylation endproducts was set forth, and corresponding diagnostic applications involving the receptors and including a specific receptor assay were also proposed.

Following this determination, the applicants herein have sought to further investigate the identity and role of advanced glycosylation endproduct receptors and possible binding partners, and any consequent diagnostic and therapeutic implications of these investigations, and it is toward this end that the present invention is directed.

SUMMARY OF THE INVENTION

In accordance with the present invention, receptor proteins are disclosed that are derived from rat liver membranes, and which recognize and bind to advance glycosylation endproducts. The receptor possesses the following characteristics:

A. It recognizes and binds with the ligands AGE-RNase and AGE-Collagen I;

B. It does not recognize and bind with the ligands FFI-BSA, formaldehyde-treated BSA, glucosamide-BSA, and acetyl LDL-BSA in a solid phase ligand blotting assay; and C. It comprises either or both of, at least two of said component proteins, the first of said proteins having a molecular mass of about 90 kD and the second of said proteins having a molecular mass of about 60 kD as determined by their migration on SDS-PAGE.

The individual proteins listed above have certain common characteristics, in that both proteins are also expressed on both rat monocytes and macrophages, and both proteins copurify from elutions based, respectively, on an AGE ligand affinity column, an anion exchange column, and a hydroxylapatite column. The proteins also have specific characteristics that distinguish them from each other, in that, when the proteins are immobilized on nitrocellulose in a solid phase assay such as that disclosed herein, the 90 kD protein does not bind to AGE-modified ligands while the 60 kD protein does.

Further, the $NH_2$-terminal partial amino acid sequences of each of the proteins have been prepared and confirm that each protein is distinguishable from the other as well as from other known protein fractions as to sequence homology. The $NH_2$-terminal partial amino acid sequence for the 90 kD protein is presented below in FIG. 11 and in SEQ ID NO:1, and comprises a single chain of 13 amino acids including two unidentified residues. The partial amino acid sequence depicted in SEQ ID NO:1 is reproduced below, with X representing the unidentified residues.

```
X Glu Val Lys Leu Pro Asp Met Val Ser Leu X Asp
1               5                  10
```

The $NH_2$-terminal partial amino acid sequence for the 60 kD protein is presented in FIG. 12 and in Sequence ID No. 2, or SEQ ID NO:2, and comprises a single chain of 22 amino acids including two unidentified residues. The partial amino acid sequence depicted in SEQ ID NO:2 is reproduced below, with X representing the unidentified residues.

```
X Gly Pro Arg Thr Leu Val Leu Leu Asp Asn Leu Asn Val Arg
1               5                       10
Arg Asp Thr His X Leu Phe Phe
15              20
```

The partial DNA sequence corresponding to the partial amino acid sequences of the proteins of the present invention or a portion thereof, or a degenerate variant of such partial DNA sequence, may be prepared as a probe to screen for complementary sequences and genomic clones in the same or alternate species, such as humans. The present invention extends to probes so prepared that may be provided for screening cDNA and genomic libraries for clones that may corrrespond to genes expressing the respective proteins. For example, the probes may be prepared with a variety of known vectors. The present invention also includes the preparation of plasmids including such vectors.

The present invention also includes full proteins having the activities noted herein, and that display the partial amino acid seqences set forth and described above and with respect to SEQ ID NO:1 and SEQ ID NO:2.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the 60 kD and the 90 kD protein, and more particularly, the complete DNA sequences determined from the partial sequences set forth above and in SEQ ID NO:1 and SEQ ID NO:2.

Likewise, the receptor proteins may be prepared alone or in operative association with another molecule or pharmaceutical agent in a form suitable for administration for either diagnostic or therapeutic purposes. The invention therefore extends to both diagnostic and pharmaceutical compositions including the receptor and/or the proteins described herein, in combination with other diagnostic reagents in the former instance, and in combination with pharmaceutically acceptable carriers, and possibly, other therapeutic agents where coadministration is deemed appropriate or desirable.

Accordingly, while the exact role that the present receptor proteins play in the recognition and removal of AGEs and in tissue remodeling is as yet largely undefined, its participation in the elicitation of certain of these activities may be strongly inferred. The receptor proteins are therefore believed to possess significant diagnostic and therapeutic capabilities in connection with conditions involving the presence and activity of advanced glycosylation endproducts.

The receptor proteins may be prepared by isolation and purification techniques from cells known to bear or produce the receptor proteins, such as rat liver cells, monocytes and peritoneal macrophage cells. The cells or active fragments likely to participate in receptor protein synthesis or to have receptor proteins associated therewith may be subjected to a series of known isolation techniques, such as for example elution of detergent-solubilized rat liver membrane proteins from an AGE-protein affinity matrix, whereupon the present receptor component proteins may be recovered. Naturally, alternate procedures for preparation of the receptor proteins are contemplated and the invention is not limited to the procedures set forth herein.

The present invention also extends to antibodies including polyclonal and monoclonal antibodies, to the receptor proteins that would find use in a variety of diagnostic and therapeutic applications. For example, the antibodies could be used to screen expression libraries to obtain genes that encode for the receptor proteins. Further, those antibodies that neutralize receptor activity could initially be employed in intact animals to better elucidate the biological role that the receptor play. Such antibodies could also participate in drug screening assays to identify alternative drugs or other agents that may exhibit the same activity as the receptor proteins.

Possible therapeutic applications of the receptor proteins would include administration in instances where it is desirable to stimulate the removal of advanced glycosylation endproducts and to correspondingly aid in the treatment of ailments where excess concentrations of AGEs may cause or exacerbate other dysfunctions or pathologies, such as diabetes.

The present invention also includes various diagnostic and therapeutic utilities predicated on the structure and activities of the receptor proteins. Diagnostic utilities include assays such as immunoassays with labeled quantities of the receptor proteins, antibodies, ligands and binding partners thereto, receptor assays, and a drug screening assay to evaluate new drugs by their ability to promote or inhibit receptor protein production or activity, as desired. The above assays could be used to detect the presence and activity of the receptor proteins or of invasive stimuli, pathology or injury the presence or absence of which would affect receptor protein production or activity.

The present invention also extends to therapeutic methods and corresponding pharmaceutical compositions based upon the receptor proteins, and materials having the same or an antagonistic activity thereto. Therapeutic methods would be based on the promotion of the activities of the receptor proteins and would extend to the treatment of diseases or dysfunctions attributable to the absence of receptor protein activity, and the concomitant excess of AGEs in the host or patient such as for example, diabetic neuropathy, renal failure, atherosclerosis, stroke, cataracts, diabetic retinopathy, and the like. This method could be effected with the receptor complex, its component complex, its component proteins, their agonists or like drugs, or materials having a promotional effect on the production of the receptor proteins in vivo.

Therapeutic compositions comprising effective amounts of the receptor proteins, their agonists, antibodies, antagonists, or like drugs, etc., and pharmaceutically acceptable carriers are also contemplated. Such compositions could be prepared for a variety of administrative protocols, including where appropriate, oral and parenteral administration. Exact dosage and dosing schedule would be determined by the skilled physician.

Diagnostic applications generally extend to a method for the measurement of protein aging both in plants and in animals, by assaying the presence, amount, location and effect of such advanced glycosylation endproducts. Assays of plant matter and animal food samples will be able for example, to assess food spoilage and the degradation of other protein material of interest so affected, while the assays of animals, including body fluids such as blood, plasma and urine, tissue samples, and biomolecules such as DNA, that are capable of undergoing advanced glycosylation, will assist in the detection of pathology or other systemic dysfunction.

Specifically, the methods comprise the performance of several competitive assay protocols, involving the analyte, a ligand and one or more binding partners to the advanced glycosylation endproducts of interest, where the binding partners are selected from the present proteins. The binding partners may be generally selected from the group consisting of rat liver cells as well as monocytes and macrophage cells having the present receptor complex and/or the component complex and/or the component proteins, cell components such as rat liver membranes, and the particular cell proteins set forth herein. The cell proteins are selected from the group consisting of the 90 kD protein derived from rat liver membranes, the 60 kD protein derived from rat liver membranes, and mixtures thereof.

The ligands useful in the present invention are generally AGE derivatives that bind to AGE binding partners. These ligands may be detected either singly and directly, or in combination with a second detecting partner such as avidin. Suitable ligands are selected from the reaction products of sugars such as glucose and glucose-6-phosphate with peptides, proteins and other biochemicals such as BSA, avidin, biotin, and enzymes such as alkaline phosphatase. Other suitable ligands may include synthetic AGEs or the reaction of the sugars directly with carriers capable of undergoing advanced glycosylation. Carriers not so capable may have a synthetic AGE coupled to them. Suitable carriers may comprise a material selected from carbohydrates, proteins, synthetic polypeptides, lipids, bio-compatible natural and synthetic resins, antigens, and mixtures thereof.

For example, standard assays based on either cell components or the cell proteins themselves and employing extract formats may be used. Each assay is capable of being based on enzyme linked and/or radiolabeled AGEs and their binding partners, including the AGE receptors disclosed herein. The broad format of assay protocols possible with the present invention extends to assays wherein no label is needed for AGE detection. For example, one of the formats contemplates the use of a bound protein-specific AGE receptor. In such instance, the analyte suspected of containing the advanced glycosylation endproducts under examination would need only to be added to the receptor, and the bound analyte could then be easily detected by a change in the property of the binding partner, such as by changes in the receptor.

The assays of the invention may follow formats wherein either the ligand or the binding partner, be it a receptor or an antibody, are bound. Likewise, the assays include the use of labels which may be selected from radioactive elements, enzymes and chemicals that fluoresce.

Accordingly, it is a principal object of the present invention to provide a receptor complex for advanced glycosylation endproducts including receptor proteins in purified form.

It is a further object of the present invention to provide probes which facilitate screening of cDNA and genomic libraries in order to clone the animal and human genes encoding the receptor proteins.

It is a still further object of the present invention to provide the complete nucleic acid and corresponding amino acid sequences in both animals and humans for the receptor complex complex and/or its component proteins.

It is a still further object of the present invention to provide agonists, antibodies, antagonists, and analogs thereof to the receptor proteins as aforesaid, compositions including pharmaceutical compositions containing them and methods for their discovery and preparation.

It is a still further object of the present invention to provide promoters of the synthesis of the receptor proteins as aforesaid, and methods for their preparation.

It is a further object of the present invention to provide a method for detecting the presence and amount of the receptor and/or advanced glycosylation endproducts in mammals in which invasive, spontaneous, or idiopathic pathological states related to excessive concentrations of advanced glycosylation endproducts are suspected to be present.

It is a further object of the present invention to provide a method and associated assay system for screening substances such as drugs, agents and the like, potentially effective in mimicking the activity of the receptor.

It is a still further object of the present invention to provide a method for the treatment of mammals to modulate the amount or activity of the receptor proteins, so as to control the consequences of such presence or activity.

It is a still further object of the present invention to provide a method for the treatment of mammals to promote the amount or activity of the receptor proteins, so as to treat or avert the adverse consequences of excessive concentrations of advanced glycosylation endproducts regardless of origin.

It is a still further object of the present invention to provide pharmaceutical compositions for use in therapeutic methods which comprise or are based upon the receptor proteins or their binding partner(s), or upon agents or drugs that control the production and/or activities of the receptor proteins.

It is a yet further object of the present invention to provide an assay for the measurement of advanced glycosylation endproducts that is capable of a broad range of alternative protocols in accordance with the method as aforesaid.

It is a yet further object of the present invention to provide an assay as aforesaid that is capable of performance without radioactive labels and that may be performed in automated fashion.

Other objects and advantages will become apparent to those skilled in the art from a consideration of the ensuing description which proceeds with reference to the following illustrative drawings.

BRIEF DESCRIPTION OF THE DRAWINGS

FIG. 5(A)—In vivo tissue distribution of $^{125}$I-AGE-RSA. Fifty µg of either $^{125}$I-AGE-rat serum albumin (AGE-RSA) (filled and striped bars) or $^{125}$I-native RSA (shaded bars) were administered i.v. to normal rats. At 10 min the animals were sacrificed, and the organs and tissues were removed and counted for radioactivity. Whole organ counts were corrected for blood-associated counts as described in Methods.

FIG. 6 depicts several graphs of an AGE-binding activity assay.

FIG. 8—(A) Ligand blot analysis of rat liver membrane proteins. Aliquots (15 µg each) of detergent-solubilized membrane proteins were electrophoresed through 8–16% acrylamide gradient gel under non-reducing conditions and eletro-transferred onto nitrocellulose filters. Using $^{125}$I-AGE-BSA (50 nM, 8.0×10$^5$ cpm/ng) as probe, specific binding was determined in the presence of 0, 25, or 150-fold excess non-labeled AGE-BSA using autoradiographic detection. Migration of molecular weight standards is shown at left.

FIG. 11 depicts the NH$_2$-terminal partial amino acid sequence prepared by blotting a quantity of gel-purified rat liver membrane protein having a molecular mass of about 90 kD (p90) onto Immobilon membranes. The amino acids are numbered from 1 to 13. This sequence is identically depicted in the SEQUENCE LISTING presented later on herein, in accordance with 37 C.F.R. 1.821–825, enacted Oct. 1, 1990, and is cumulatively and alternately referred to as SEQ ID NO:1.

FIG. 12 depicts the NH$_2$-terminal partial amino acid sequence prepared by blotting a quantity of gel-purified rat liver membrane protein having a molecular mass of about 60 kD (p60) onto Immobilon membranes. The amino acids are numbered from 1 to 22. This sequence is identically depicted in the SEQUENCE LISTING presented later on herein, in accordance with 37 C.F.R. 1.821–825, enacted Oct. 1, 1990, and is cumulatively and alternately referred to as SEQ ID NO:2.

DETAILED DESCRIPTION OF THE PREFERRED EMBODIMENTS

Figure 1:
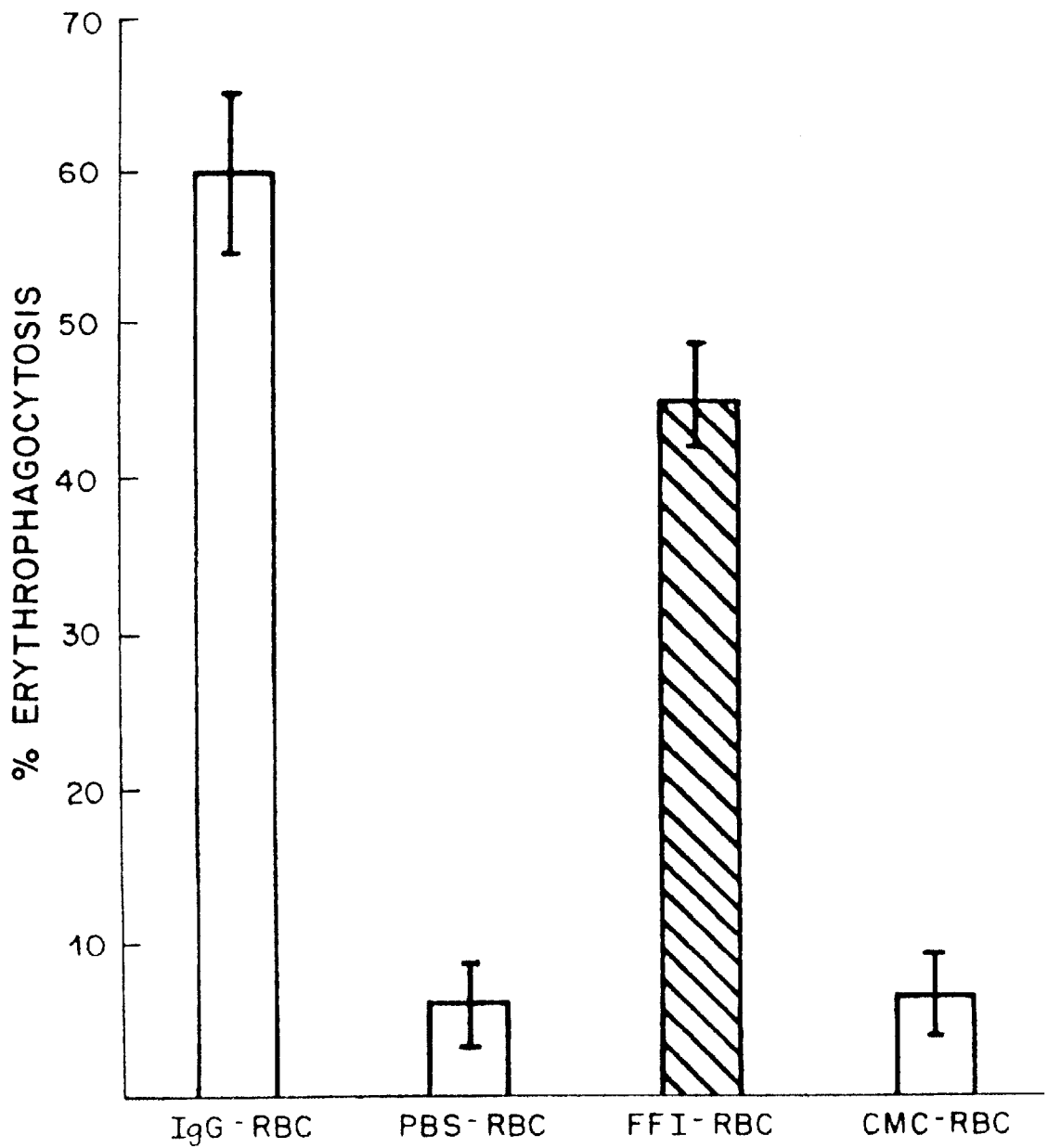
FIG. 1 is a graph depicting the relative binding and uptake of red blood cells modified with various agents, and illustrating a primary aspect of the present invention.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984).

Therefore if appearing herein, the following terms shall have the definitions set out below.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. NH2 refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

As used throughout the present application, the terms "receptor complex" and "receptor complex/component protein(s)" includes both the singular and plural and contemplates the existence of a single receptor structure comprised as all or part thereof, of the individual proteins defined herein, or a plurality of receptor structures respectively constituted in whole or in part by the individual proteins. This definition is therefore to be explicitly distinguished from the definition that may be inferred from the term as it appears in the manuscript by Yang et al. from which the present application is drawn in part.

An "antibody" is any immunoglobulin, including antibodies and fragments thereof, such as Fab, F(ab')$_2$ or dAb, that binds a specific epitope. The term encompasses, inter alia, polyclonal, monoclonal, and chimeric antibodies, the last mentioned described in further detail in U.S. Pat. Nos. 4,816,397 and 4,816,567. An antibody preparation is reactive for a particular antigen when at least a portion of the individual immunoglobulin molecules in the preparation recognize (i.e., bind to) the antigen. An antibody preparation is non-reactive for an antigen when binding of the individual immunoglobulin molecules in the preparation to the antigen is not detectable by commonly used methods.

In its broadest aspect, the present invention relates to receptor complex proteins as defined herein that are derived from rat liver membranes, as well as monocytes and peritoneal macrophage cells, and that recognize and bind advanced glycosylation endproducts. The receptor has the following characteristics:

A. It recognizes and binds with the ligands AGE-RNase and AGE-Collagen I;

B. It does not recognize and bind with the ligands FFI-BSA, formaldehyde-treated BSA, glucosamide-BSA, and acetyl LDL-BSA in a solid phase ligand blotting assay; and C. It comprises either or both of at least two proteins (the conponent proteins), the first of said proteins having a molecular mass of about 90 kD and the second of said proteins having a molecular mass of about 60 kD as determined by their migration on SDS-PAGE.

The receptor proteins have certain common characteristics, in that both proteins are also expressed on both rat monocytes and macrophages, and both proteins copurify from elutions based, respectively, on an AGE ligand affinity column, an anion exchange column, and a hydroxylapatite column. The proteins also have specific characteristics that distinguish them from each other, in that, when the proteins are immobilized on nitrocellulose in a solid phase assay, the 90 kD protein does not bind to AGE-modified ligands while the 60 kD protein does.

As set forth earlier, the $NH_2$-terminal partial amino acid sequences of each of the component proteins have been prepared and confirm that each protein bears no homology with the other as well as with other known protein fractions. The $NH_2$-terminal partial amino acid sequence for the 90 kD protein is presented below and in SEQ ID NO:1, and comprises a single chain of 13 amino acids including two unidentified residues represented by "X".

```
  X Glu Val Lys Leu Pro Asp Met Val Ser Leu X Asp
  1               5                  10
```

The $NH_2$-terminal partial amino acid sequence for the 60 kD protein is presented below in SEQ ID NO:2, and comprises a single chain of 22 amino acids including two unidentified residues, likewise represented by "X".

```
 X Gly Pro Arg Thr Leu Val Leu Leu Asp Asn Leu Asn Val Arg
 1             5                    10
 Arg Asp Thr His X Leu Phe Phe
 15                  20
```

As stated earlier, the partial DNA sequence corresponding to the partial amino acid sequences of the proteins of the present invention or a portion thereof, may be prepared as a probe to screen for complementary sequences and genomic clones in the same or alternate species, such as humans. The present invention extends to probes so prepared that may be provided for screening cDNA and genomic libraries for clones that may corrrespond to genes expressing the respective proteins. For example, the probes may be prepared with a variety of known vectors, such as phage I vectors. The present invention also includes the preparation of plasmids including such vectors.

The present invention also includes full proteins having the activities noted herein, and that display the partial amino acid seqences set forth and described above and with respect to SEQ ID NO:1 and SEQ ID NO:2.

As stated earlier, the receptor proteins may be prepared by isolation and purification from cells known to bear or produce the proteins, such as rat liver cells, monocytes and peritoneal macrophage cells. The cells or active fragments likely to participate in receptor complex/protein synthesis or to have receptor proteins associated therewith may be subjected to a series of known isolation techniques, such as for example elution of detergent-solubilized rat liver membrane proteins from an AGE-protein affinity matrix, whereupon the proteins may be recovered. A specific protocol is set forth by way of illustration in Example III, later on herein. The present invention naturally contemplates alternate means for preparation of the proteins, including stimulation of complex producer cells with promoters of receptor protein synthesis followed by the isolation and recovery of the receptor proteins as indicated above, as well as chemical synthesis, and the invention is accordingly intended to cover such alternate preparations within its scope.

The present invention also extends to antibodies including polyclonal and monoclonal antibodies, to the receptor proteins that would find use in a variety of diagnostic and therapeutic applications. For example, the antibodies could be used to screen expression libraries to obtain the gene that encodes either the receptor complex or proteins. Further, those antibodies that neutralize receptor protein activity could initially be employed in intact animals to better elucidate the biological role that the receptor proteins play. Such antibodies could also participate in drug screening assays to identify alternative drugs or other agents that may exhibit the same activity as the receptor proteins.

Both polyclonal and monoclonal antibodies to the receptor complex are contemplated, the latter capable of preparation by well known techniques such as the hybridoma technique, utilizing, for example, fused mouse spleen lymphocytes and myeloma cells. Immortal, antibody-producing cell lines can also be created by techniques other than fusion, such as direct transformation of B lymphocytes with oncogenic DNA, or transfection with Epstein-Barr virus. Specific avian polyclonal antibodies were raised herein and are set forth in Example III. Naturally, these antibodies are merely illustrative of antibody preparations that may be made in accordance with the present invention.

As the receptor proteins appear to play a role in the recognition and removal of advanced glycosylation endproducts in vivo, the present invention contemplates both diagnostic and therapeutic applications for these agents. Accordingly, the receptor proteins may be prepared for use in a variety of diagnostic methods, set forth in detail hereinafter, and may be labeled or unlabeled as appropriate. Likewise, the receptor proteins may be prepared for administration in various scenarios for therapeutic purposes, in most instances to assist in reducing the concentration of AGEs in vivo.

The receptor proteins may be prepared in a therapeutically effective concentration as a pharmaceutical composition with a pharmaceutically acceptable carrier. Other compatible pharmaceutical agents may possibly be included, so that for example certain agents may be simultaneously coadministered. Also, the receptor proteins may be associated with or expressed by a compatible cellular colony, and the resulting cellular mass may then be treated as a therapeutic agent and administered to a patient in accordance with a predetermined protocol. Numerous therapeutic formulations are possible and the present invention contemplates all such variations within its scope. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, catheterizations and the like.

Corresponding therapeutic utilities take advantage of the demonstrated activity of the proteins toward advanced glycosylation endproducts. Thus, to the extent that the in vivo recognition and removal of AGEs serves to treat ailments attributable to their presence in an excess concentration, the administration of the present receptor proteins comprises an effective therapeutic method. Such conditions as diabetic nephropathy, renal failure and the like may be treated and/or averted by the practice of the therapeutic methods of the present invention. Average quantities of the active agent may vary and in particular should be based upon the recommendations and prescription of a qualified physician or veterinarian, with an exemplary dosage regimen extending to up to about 25 mg/kg/day.

The present invention also relates to a variety of diagnostic applications, including methods for the measurement of the presence and amount of advanced glycosylation endproducts in both plants and animals, including humans. The methods comprise assays involving in addition to the analyte, one or more binding partners of the advanced glycosylation endproducts, and one or more ligands.

Accordingly, the present assay method broadly comprises the steps of:

A. preparing at least one biological sample suspected of containing said advanced glycosylation endproducts;

B. preparing at least one corresponding binding partner directed to said samples, wherein said binding partner includes or is selected from the present receptor proteins, and mixtures;

C. placing a detectible label on a material selected from the group consisting of said samples, a ligand to said binding partner and said binding partner;

D. placing the labeled material from Step C in contact with a material selected from the group consisting of the material from Step C that is not labeled; and E. examining the resulting sample of Step D for the extent of binding of said labeled material to said unlabeled material.

Suitable analytes may be selected from plant matter, blood, plasma, urine, cerebrospinal fluid, lymphatic fluid, and tissue; and the compounds FFI and AFGP, individually and bound to carrier proteins such as the protein albumin. The analyte may also comprise a synthetically derived advanced glycosylation endproduct which is prepared, for example, by the reaction of a protein or other macromolecule with a sugar such as glucose, glucose-6-phosphate, or others. This reaction product could be used alone or could be combined with a carrier in the same fashion as the FFI-albumin complex.

The carrier may be selected from the group consisting of carbohydrates, proteins, synthetic polypeptides, lipids, biocompatible natural and synthetic resins, antigens and mixtures thereof.

As stated earlier, the present invention seeks by means of the present receptor proteins to diagnose both the degradative effects of advanced glycosylation of proteins in plants and the like, and the adverse effects of the buildup of advanced glycosylation endproducts in animals. Such conditions as age- or diabetes-related hardening of the arteries, skin wrinkling, arterial blockage, and diabetic, retinal and renal damage in animals all result from the excessive buildup or trapping that occurs as advanced glycosylation endproducts increase in quantity. Therefore, the diagnostic method of the present invention seeks to avert pathologies caused at least in part by the accumulation of advanced glycosylation endproducts in the body by monitoring the amount and location of such AGEs.

Likewise, as advanced glycosylation endproducts may be measured by the extent that they bind to receptors on cells from a variety of sources, the assays of the present invention are particularly suited to design and performance around this activity. For example, in a typical competitive assay in accordance with the present invention, the present receptor and/or cellular material bearing the receptor may be combined with the analyte and the ligand and the binding activity of either or both the ligand or the analyte to the receptor may then be measured to determine the extent and presence of the advanced glycosylation endproduct of interest. In this way, the differences in affinity between the components of the assay serves to identify the presence and amount of the AGE.

The present invention also relates to a method for detecting the presence of stimulated, spontaneous, or idiopathic pathological states in mammals, by measuring the corresponding presence of advanced glycosylation endproducts. More particularly, the activity of AGEs may be followed directly by assay techniques such as those discussed herein, through the use of an appropriately labeled quantity of at least one of the binding partners to AGEs as set forth herein. Alternately, AGEs can be used to raise binding partners or antagonists that could in turn, be labeled and introduced into a medium to test for the presence and amount of AGEs therein, and to thereby assess the state of the host from which the medium was drawn.

Thus, both AGE receptors and any binding partners thereto that may be prepared, are capable of use in connection with various diagnostic techniques, including immunoassays, such as a radioimmunoassay, using for example, a receptor or other ligand to an AGE that may either be unlabeled or if labeled, then by either radioactive addition, reduction with sodium borohydride, or radioiodination.

In an immunoassay, a control quantity of a binding partner to advanced glycosylation endproducts may be prepared and optionally labeled, such as with an enzyme, a compound that fluoresces and/or a radioactive element, and may then be introduced into a tissue or fluid sample of a mammal believed to be undergoing invasion. After the labeled material or its binding partner(s) has had an opportunity to react with sites within the sample, the resulting mass may be examined by known techniques, which may vary with the nature of the label attached.

The presence of AGE activity in animals and plants can be ascertained in general by immunological procedures are which utilize either a binding partner to the advanced glycosylation endproduct or a ligand thereto, optionally labeled with a detectable label, and further optionally including an antibody $Ab_1$ labeled with a detectable label, an antibody $Ab_2$ labeled with a detectable label, or a chemical conjugate with a binding partner to the advanced glycosylation endproduct labeled with a detectable label. The procedures may be summarized by the following equations wherein the asterisk indicates that the particle is labeled, and "BP" in this instance stands for all binding partners of advanced glycosylation endproduct(s) under examination:

A. $BP^* + Ab_1 = BP^*Ab_1$

B. $BP + Ab^* = BPAb_1^*$

C. $BP + Ab_1 + Ab_2^* = BPAb_1Ab_2^*$

D. $Carrier^*BP + Ab_1 = Carrier^*BPAb_1$

These general procedures and their application are all familiar to those skilled in the art and are presented herein as illustrative and not restrictive of procedures that may be utilized within the scope of the present invention. The "competitive" procedure, Procedure A, is described in U.S. Pat. Nos. 3,654,090 and 3,850,752. Optional procedure C, the "sandwich" procedure, is described in U.S. Pat. Nos. RE 31,006 and 4,016,043, while optional procedure D is known as the "double antibody", or "DASP" procedure.

A further alternate diagnostic procedure employs multiple labeled compounds in a single solution for simultaneous radioimmune assay. In this procedure disclosed in U.S. Pat. No. 4,762,028 to Olson, a composition may be prepared with two or more analytes in a coordinated compound having the formula: radioisotope-chelator-analyte.

In each instance, the advanced glycoslation endproduct forms complexes with one or more binding partners and one member of the complex may be labeled with a detectable label. The fact that a complex has formed and, if desired, the amount thereof, can be determined by the known applicable detection methods.

With reference to the use of an AGE antibody as a binding partner, it will be seen from the above that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. Where used and for purposes of this description, $Ab_1$ will be referred to as a primary or anti-advanced glycosylation endproduct antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

Suitable radioactive elements may be selected from the group consisting of $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. In the instance where a radioactive label, such is prepared with one of the above isotopes is used, known currently available counting procedures may be utilized.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the advanced glycosylation endproducts, their binding partners or carrier molecules by reaction with bridging molecules such as carbodiimides, diisocyanates, glutaraldehyde and the like. Also, and in a particular embodiment of the present invention, the enzymes themselves may be modified into advanced glycosylation endproducts by reaction with sugars as set forth herein.

Many enzymes which can be used in these procedures are known and can be utilized. The preferred are peroxidase, β-glucuronidase, β-D-glucosidase, β-D-galactosidase, urease, glucose oxidase plus peroxidase, hexokinase plus GPDase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850, 752; and 4,016,043 are referred to by way of example for their disclosure of alternative labeling material and methods.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The present invention includes assay systems that may be prepared in the form of test kits for the quantitative analysis of the extent of the presence of advanced glycosylation endproducts. The system or test kit may comprise a labeled component prepared by one of the radioactive and/or enzymatic techniques discussed herein, coupling a label to a binding partner to the advanced glycosylation endproduct such as a receptor or ligand as listed herein; and one or more additional immunochemical reagents, at least one of which is a free or immobilized ligand, capable either of binding with the labeled component, its binding partner, one of the components to be determined or their binding partner(s).

In a further embodiment of this invention, commercial test kits suitable for use by a medical specialist may be prepared to determine the presence or absence of advanced glycosylation endproducts. In accordance with the testing techniques discussed above, one class of such kits will contain at least labeled AGE, or its binding partner as stated above, and directions, of course, depending upon the method selected, e.g., "competitive", "sandwich", "DASP" and the like. The kits may also contain peripheral reagents such as buffers, stabilizers, etc.

For example, a first assay format contemplates a bound receptor to which are added the ligand and the analyte. The resulting substrate is then washed after which detection proceeds by the measurement of the amount of ligand bound to the receptor. A second format employs a bound ligand to which the receptor and the analyte are added. Both of the first two formats are based on a competitive reaction with the analyte, while a third format comprises a direct binding reaction between the analyte and a bound receptor. In this format a bound receptor-specific carrier or substrate is used. The analyte is first added after which the receptor is added, the substrate washed, and the amount of receptor bound to the substrate is measured.

More particularly, the present invention includes the following protocol within its scope:

A method for determining the amount of advanced glycosylation endproducts in an analyte comprising:

A. providing a sample of monocytes bearing the present receptor complex/component protein(s);

B. inoculating said sample with a known advanced glycosylation endproduct bound to a whole cell; and C. counting the whole cells of Step B that are bound to and/or internalized by said sample.

The specific protocol set forth above is illustrated in the examples that follow later on herein, and reflects the broad latitude of the present invention. All of the protocols disclosed herein may be applied to the qualitative and quantitative determination of advanced glycosylation endproducts and to the concomitant diagnosis and surveillance of pathologies in which the accretion of advanced glycosylation endproducts is implicated. Such conditions as diabetes and the conditions associated with aging, such as atherosclerosis and skin wrinkling represent non-limiting examples, and accordingly methods for diagnosing and monitoring these conditions are included within the scope of the present invention.

Accordingly, a test kit may be prepared for the demonstration of the presence and activity of AGEs, comprising:

(a) a predetermined amount of at least one labeled immunochemically reactive component obtained by the direct or indirect attachment of an advanced glycoslation endproduct binding partner comprising the present receptor protein(s) or a specific binding partner thereto, to a detectable label;

(b) other reagents; and (c) directions for use of said kit.

More specifically, the diagnostic test kit may comprise:

(a) a known amount of a binding partner as described above, or a ligand thereof, generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may comprise:

(a) a labeled component which has been obtained by coupling the above binding partner to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the advanced glycosylation endproduct and the binding partner.

The present invention will be better understood from a consideration of the following illustrative examples and data. Accordingly, Examples I and II presented in parent application Ser. No. 453,958 confirm the basic hypothesis that the in vivo recognition and removal of AGEs is receptor mediated, and Examples III presents the investigations and experiments that have resulted in the identification of the liver-derived AGE receptors of the present invention.

EXAMPLE I

In this example, the existence of the receptor-mediated clearance system of advanced glycosylation endproducts that underlies the present assay was initially explored, in part, by the performance of a competitive phagocytosis assay was conducted with whole monocytes. A full review of the details of the experimental procedures involved is presented in U.S. Pat. No. 4,900,747, and reference may be made thereto for such purpose.

In this example, human red blood cells (RBCs) were collected and isolated, and separate quantities were prepared to facilitate the performance of the assay. Specifically, a quantity of RBCs were opsonized by incubation with an appropriate antiserum. A further quantity was bound to the advanced glycosylation endproduct FFI by a carbodiimide bond, and additional RBCs were separately glycosylated by reactions with glucose, glucose-6-phosphate, xylose and arabinose, respectively. Lastly, AGE-BSA and human monocytes were prepared. Phagocytosis assays proceeded by the incubation of the RBCs with the monocyte cultures followed by fixation of the sample wells and lastly counting under 40× phase microscopy.

An FFI-RBC half life assay was also conducted with Balb/c mice that were inoculated with FFI-RBC suspensions labeled with $^{51}Cr$. The labeled cells were washed at least four times to remove unbound isotope. Twelve Balb/c mice were then injected intravenously with 200 µl RBC suspension. Each sample was administered in three Balb/c mice. At appropriate time intervals the mice were bled (0.2 ml) and radioactivity levels were measured by counting.

RESULTS

Maximum binding of red cells was observed on Day-7 of monocyte incubation in vitro. Maximum binding and endocytosis of FFI-RBC was complete within 30–45 minutes while opsonized cells were maximally bound within 15 minutes. At the end of one hour incubation of FFI-coupled RBC's with cultured human monocytes, per cent phagocytosis and phagocytic index were estimated. As shown in FIG. 1, % erythrophagocytosis of FFI-modified red cells (55%) and IgG-coated red cells (70%) were significantly higher than that of control PBS-treated cells (4%). Similarly the phagocytic index of FFI-treated RBC's was greatly elevated (3.4) as compared to normal controls (1.2).

Figure 2:
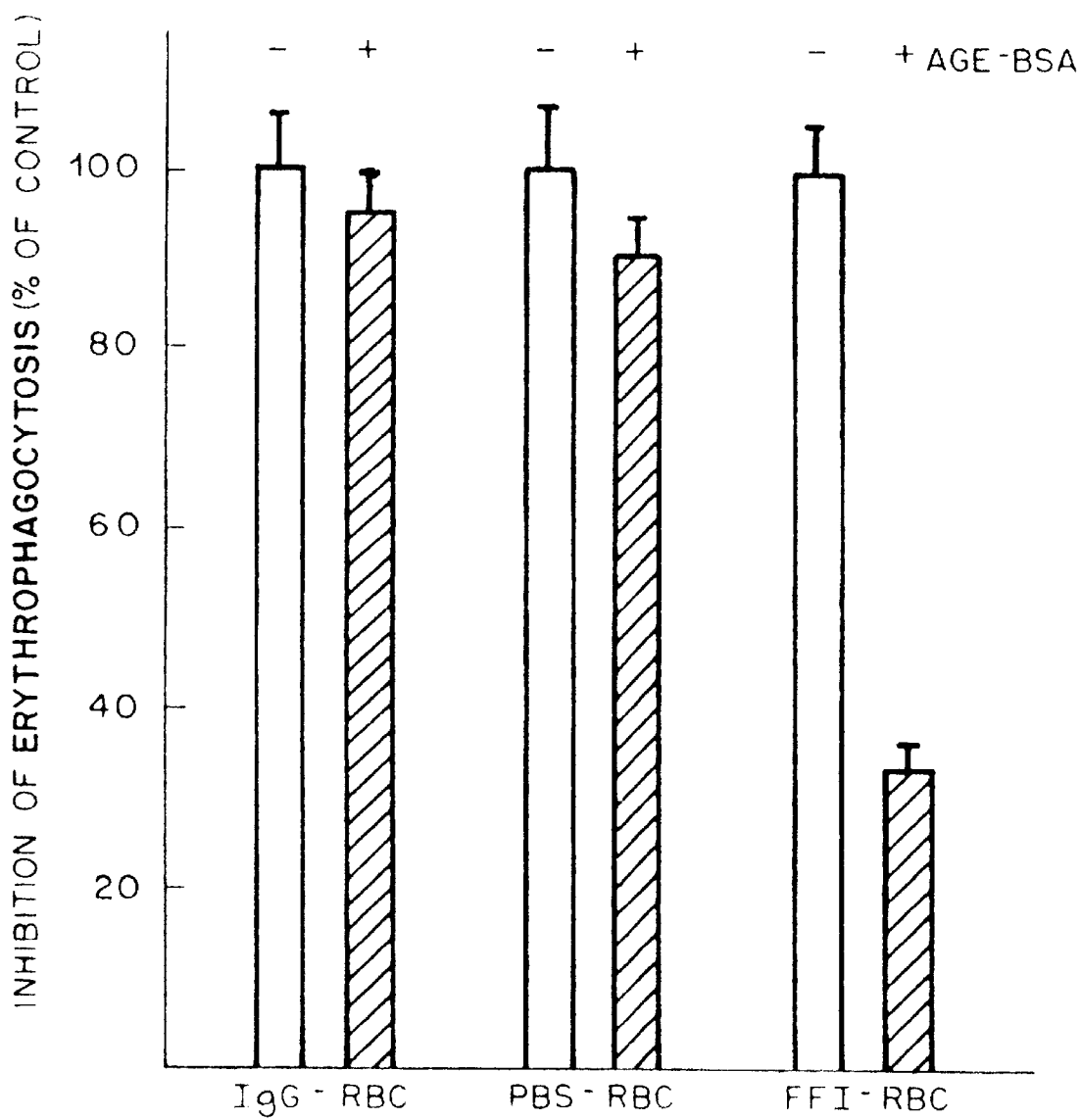
FIG. 2 is a graph illustrating an assay in accordance with the present invention by the competitive inhibition in red blood cell binding caused by the introduction into a sample of an agent capable of stimulating red blood cells to increase their activity of recognition and removal of advanced glycosylation endproducts.
Figure 3:
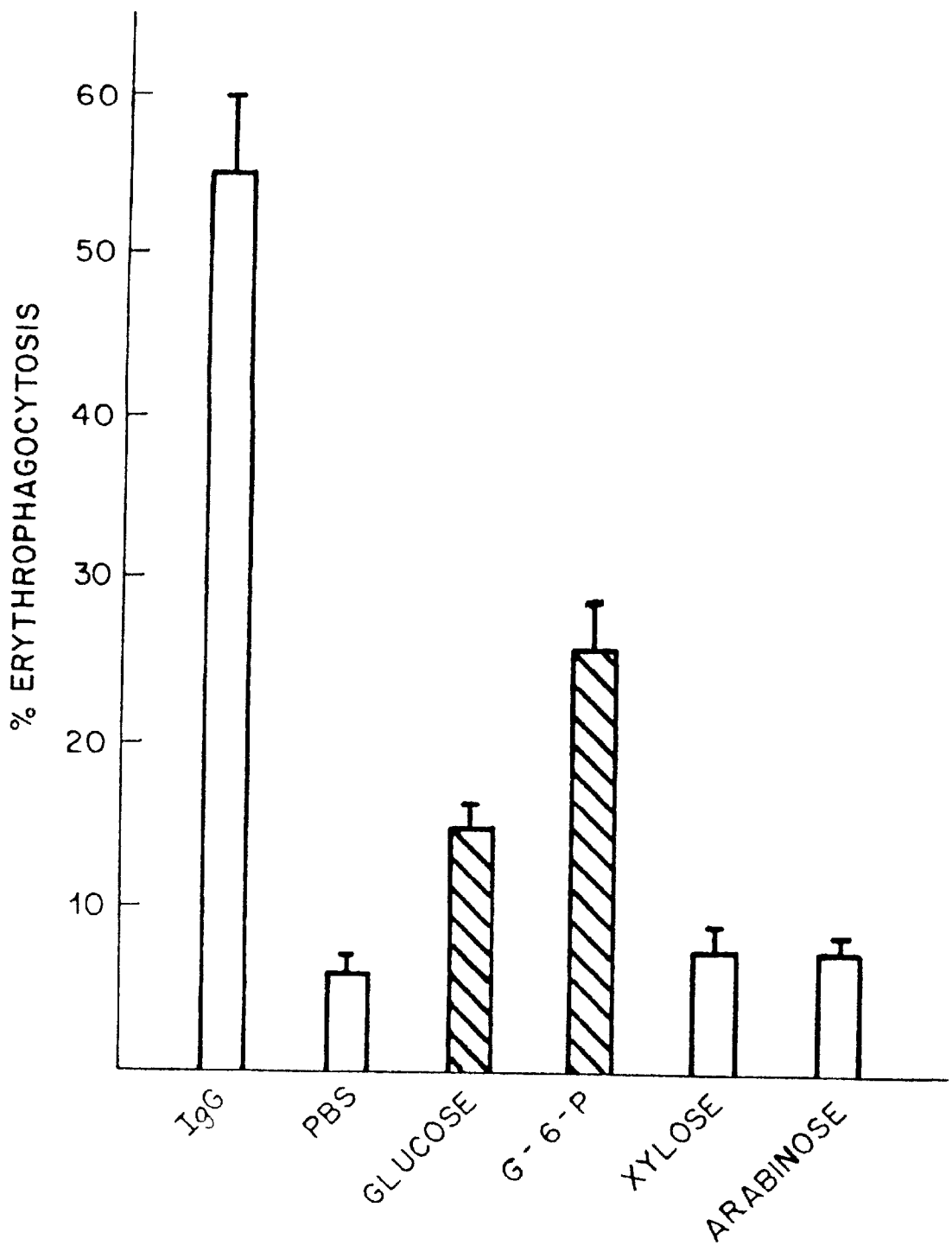
FIG. 3 is a bar graph illustrating the comparative uptake and degradation of advanced glycosylation endproducts by mouse macrophages exposed to various stimulator compounds.

In order to establish the specificity of the interaction of FFI-RBC's with the human monocytes, competition experiments were carried out in which binding and ingestion of red cells was observed in the absence and presence of AGE-BSA, prepared as described in Methods (Vlassara et al., supra.). As shown in FIG. 2, the addition of AGE-BSA at concentrations of 500 mg/ml inhibited the FFI-RBC binding by more than 70% of the control. In contrast, AGE-BSA did not inhibit opsonized or PBS-treated red cells, even at maximal concentrations (1 mg/ml). These data suggested that FFI-modified red cells were recognized and bound specifically by the monocyte AGE-binding site, and consequently confirmed the operability of the present assay.

DISCUSSION

The above tests extend previous observations on the recognition of advanced glycosylation endproducts (AGE) by a specific monocyte/macrophage receptor, and present evidence that such adducts once attached chemically or formed in vitro on the surface of intact human cells can induce cell binding and ingestion by normal human monocytes. The experiments establish the development of a competitive receptor-based assay for AGEs measuring by way of illustration herein, AGE-red cell binding in the presence of large excess of AGE-BSA (Vlassara et al., supra.).

EXAMPLE II

This example comprises a series of experiments that were initially performed to measure the ability of agents to stimulate phagocytic cells to stimulate uptake and degradation of endproducts (AGEs), and thereby further confirmed the hypothesis that this activity is receptor-mediated.

Several AGEs were prepared using the same procedure as disclosed in Example I, above. Accordingly, FFI-HA was prepared as described and quantities were bound to both human and bovine albumin. A water soluble carbodiimide was used to attach the acid moiety of the FFI-HA to an amino group on the protein. After preparation, the conjugate was purified and then used in vitro to stimulate macrophages, by incubation for from 4 to 24 hours.

The AGEs that were to be observed for uptake and degradation were appropriately radiolabeled so that they could be traced. Thereafter, the stimulated macrophages were tested by exposure to the radiolabeled AGEs following exposure to various agents to measure the effect that these agents had on the ability of the macrophages to take up and degrade the labeled AGEs. The above procedures conform to the protocol employed by Vlassara et al., supra, and confirmed that a competitive assay based on a cellular receptor for AGEs is feasible.

Figure 4:
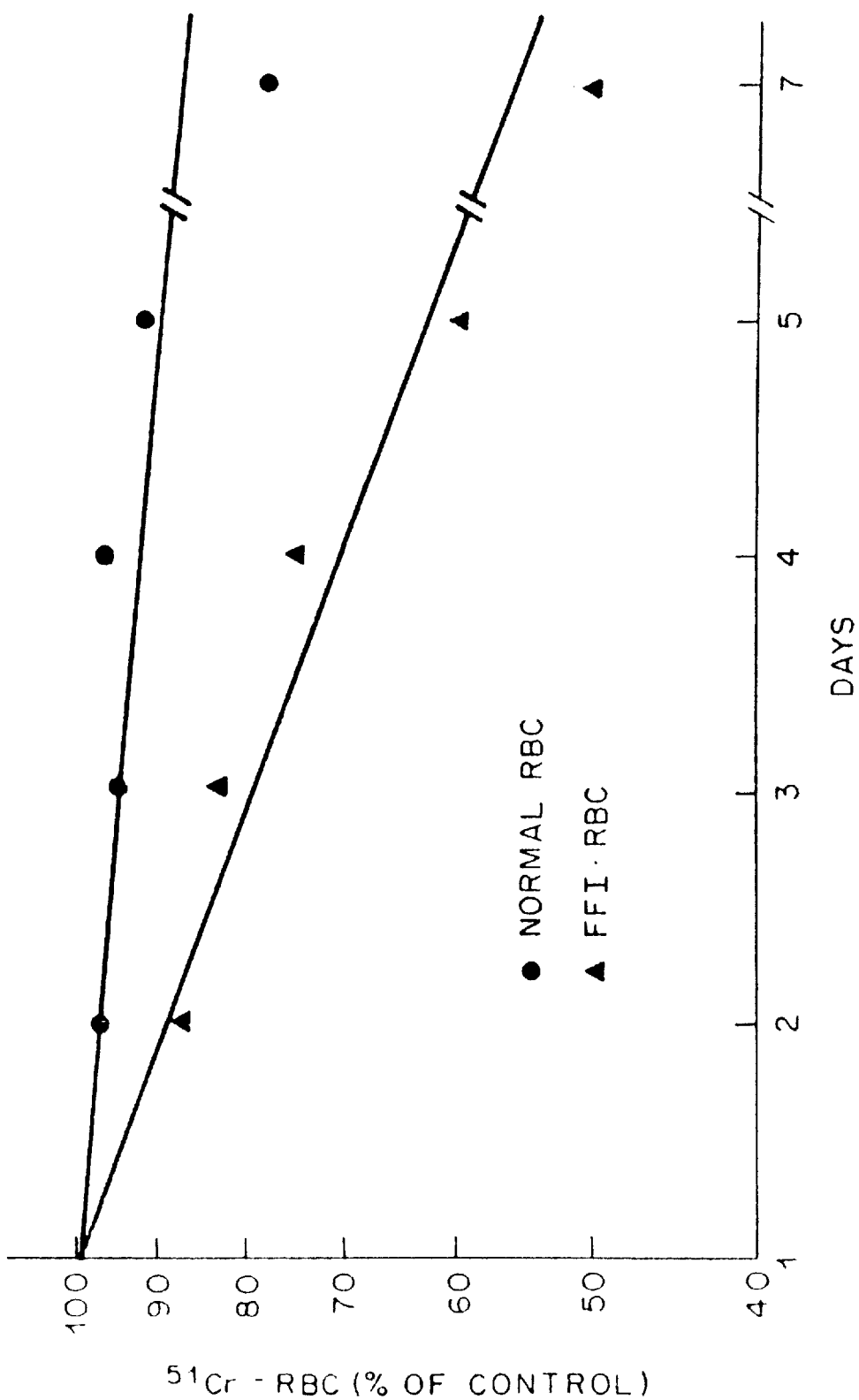
FIG. 4 is a bar graph illustrating data similar to that set forth in FIG. 3, with respect to one day old human monocytes.

It was also demonstrated that monocyte or macrophage cells can also be stimulated by AGE-carrier molecules which result in cells with enhanced ability to bind, internalize and degrade other AGE-molecules. AGE-carrier molecules are made, for example, from the reaction of glucose or glucose-6-phosphate with albumin. After purification of the reaction product, the AGE-albumin uptake of AGE-macromolecules demonstrated as in (A) above. AGE-BSA (prepared from the incubation of glucose-6-phosphate with albumin for 6–8 weeks) at 0.1 mg/ml demostrates a stimulatory effect on AGE-BSA uptake by human monocytes (FIG. 4, bar AA), and shows a slight stimulation at higher concentrations (bars BB and CC). This observation further supports the role of these ligands in conjunction with cellular receptors and point to the application of these agents in a competitive AGE assay protocol.

EXAMPLE III

The following example discloses the purification from rat liver, and partial amino acid sequencing, of two membrane proteins of approximately 60 and 90 kD, respectively, that bind AGE-modified proteins. Both of the proteins presented are expressed on the surface of rat monocytes and resident peritoneal macrophages, suggesting a relationship to the AGE-receptor system earlier identified on these cells. The proteins are believed to be involved in tissue repair and remodelling.

MATERIALS AND METHODS

Chemicals and reagents. Bovine serum albumin (BSA) (Fraction V), bovine ribonuclease, glucosamide-BSA, glucose-6-phosphate and collagen I were purchased from Sigma Chemical Co. (St. Louis, Mo.). Triton X-114 and Triton X-100 were purchased from Boehringer Mannheim Biochemicals (Indianapolis, Ind.). Sodium $^{125}$iodide was obtained from New England Nuclear (Boston, Mass.). Nitrocellulose membranes were from Schliecher & Schuell (Keene, N.H.). CNBr-activated Sepharose 4B was purchased from Pierce (Rockford, Ill.). LDL and acetyl-LDL were the generous gift of Dr. David Via (Baylor College of Medicine, Houston, Tex.). 2-(2-furoyl)-4(5)-(2-furanyl)-1H-imidazole (FFI) and its derivative, FFI-1-hexanoic acid (FFI-HA) were kindly provided by Dr. Peter Ulrich (Geritech Inc., Northvale, N.J.).

Preparation of AGE-proteins and formaldehyde-modified proteins. AGE-BSA, AGE-RSA, AGE-ribonuclease and AGE-collagen I were generated by standardized methods as previously described in detail. In brief, each protein solution (25 mg/ml) was incubated with either 0.5M glucose or glucose-6-phosphate in 100 mM phosphate buffer (pH 7.4) at 37° C. for six weeks under sterile conditions, and then low molecular weight reactants were removed by dialysis against phosphate buffered saline (PBS; 20 mM sodium phosphate buffer containing 0.15M NaCl, pH 7.4). FFI-HA was coupled to BSA with the water-soluble carbodiimide, EDAC, as described previously. Characteristic fluorescence of the AGE-proteins was observed at 450 nm upon excitation at 390 nm. Formaldehyde-modified BSA was prepared as described, by incubating BSA in 0.1M sodium carbonate buffer (pH 10) with 0.33M formaldehyde at 37° C. for 5 hours, followed by extensive dialysis against PBS. All protein concentrations were determined by the method of Bradford. Protein and AGE-protein preparations were radio-labeled with [$^{125}$I] by the Iodo-Gen method for example, 2 mg of AGE-BSA were incubated with 25 mCi carrier-free [$^{125}$I] in an Iodogen-coated glass vial at room temperature for 45 min. In order to separate free from bound [$^{125}$I], the sample was fractionated by Sephadex G-25M column chromatography and dialysis against PBS, until at least 98% of the $^{125}$I was trichloroacetic acid-precipitable. The specific radioactivity of the labeled $^{125}$I-AGE-BSA was between 8,000–15,000 cpm/ng protein.

BSA and AGE-BSA Sepharose were prepared by reacting either BSA or AGE-BSA (25 mg/ml) with CNBr-Sepharose gel (5 ml/g of dry powder) according to the manufacturers instructions, in coupling buffer (0.1M NaHCO$_3$, 0.5M NaCl, pH 8.3). The mixture was rotated for 2 h at room temperature. Excess ligand was washed from the resin with coupling buffer and then with Tris-HCl buffer (0.1M, pH 8.0) for 2 h at room temperature to block remaining active groups. The resin was then washed with three cycles of sodium acetate buffer (0.1M, pH 4) containing NaCl (0.5M), followed by Tris-HCl buffer (0.1M, pH 8) containing NaCl (0.5M), and stored at 4°–8° C.

In Vivo Studies. For tissue distribution studies, AGE-rat serum albumin (AGE-RSA) was prepared as described above, and radioiodinated to a specific activity of $8.3 \times 10^5$ cpm/$\mu$g. Similarly, normal RSA was iodinated to a specific activity of $6.2 \times 10^5$ cpm/$\mu$g. Freshly drawn rat red blood cells (RBC) were labeled with $^{51}$Cr to allow subsequent correction for tissue counts for blood-associated radioactivity. Approximately 1 mCi of $^{51}$Cr was added to 10 ml RBC, mixed thoroughly and allowed to incubate for 30 min at room temperature prior to washing with PBS containing 1% BSA and 0.1% dextrose until supernatant radioactivity was less than 1% of that in the packed RBC. Buffer was added to labeled RBC to obtain a hematocrit of 40% and the labeled RBC were used immediately.

To determine the tissue distribution of AGE-ligands, normal male Sprague-Dawley rats (200 g) were divided into groups of five, and anesthetized with sodium pentobarbital (40 mg/kg). All animals received an injection of $^{51}$Cr-RBC (0.65 ml, i.v.) five minutes prior to the labeled ligand. The indicated groups of rats received either $^{125}$I-AGE-RSA (50 $\mu$g in 0.1 ml, i.v.) or an identical amount of $^{125}$I-normal RSA. At the indicated time intervals, 0.5 ml aliquots of blood were drawn and various organs were removed and counted for radioactivity. The specificity of AGE-ligand uptake in various organs was assessed by injecting groups of animals with excess non-labeled AGE-BSA (5 mg) two minutes prior to administration of 50 $\mu$g of $^{125}$I-AGE-BSA. After 5, 20, and 60 minutes, 0.5 ml blood samples were collected, animals were sacrificed, and various organs and tissues were collected and counted for radioactivity. The red blood cells were lysed with water, and protein was precipitated with 20% TCA. The organs were weighed, homogenized with a hand homogenizer, protein was precipitated with 20% TCA and counted for radioactivity. The tissue-to-blood isotope ratio (TBIR) was calculated by the formula TBIR=[$^{125}$I/$^{51}$Cr in tissue]/[$^{125}$I/$^{51}$Cr in blood]. TBIR is a dimensionless index of the degree to which any tissue sample has sequestered labeled ligand relative to the blood.

Solubilization and fractionation of hepatic membrane proteins. Liver membranes were prepared according to the method of Thom et al. with some modifications. For a typical membrane preparation, 14 grams of rat liver were homogenized in 80 ml TNE buffer [50 mM Tris-HCl buffer (pH 8.0), containing 150 mM NaCl, 0.1 mM EDTA, and 23 $\mu$g/ml phenylmethylsulfonyl fluoride (PMSF)] and centrifuged for 10 min at 3000×g. The supernate was layered on top of a solution of 40% sucrose in TNE buffer, and centrifuged at 24,000×g for 1 h at 4° C. The membranes were collected from the interface with a Pasteur pipette. The membrane preparation was solubilized in TNE buffer containing 2% Triton X-114 at 4° C. and clarified by centrifugation for 30 min at 100,000×g. The supernate was then warmed to 30° C. and the detergent phase, aqueous phase and detergent-insoluble pellet were separated according to the phase separation method described by Bordier. The resulting detergent phase was either used directly for purification of AGE-binding proteins or diluted 1:10 with PBS containing 2% Triton X-100 and 2 mM PMSF. This material (D-phase) was frozen at −80° C. until further use.

In Vitro solid-phase AGE binding assay. AGE-binding activity was determined by a modified version of solid-phase binding assay developed for the IL-1 receptor. Aliquots of detergent-solubilized membrane proteins were blotted onto grid-marked nitrocellulose (NC) membranes. The blots were dried at room temperature and could be stored at room temperature for several weeks without apparent loss of binding activity. The NC membranes were cut into small squares (0.9 cm$^2$) with the immobilized protein at the center and distributed in 24-well trays (Costar, Cambridge, Mass.). Immobilized protein was reconstituted in PBS, pH 7.4, containing 0.5% Triton X-100 for 30–60 min at room temperature. The blots were subsequently incubated in blocking buffer (PBS, pH 7.4, containing 2% BSA, 0.2% Triton X-100 and 1 mM MgCl$_2$) for 2 h with agitation at 4° C. Specific ligand binding was carried out by adding 50–100 nM $^{125}$I-AGE-BSA directly to the blocking buffer and agitating at 4° C for a further 1.5 h. The NC membranes were transferred to a new tray and rinsed quickly 3 times with PBS containing 0.2% Triton X-100, followed by two additional 10 min. washings with PBS. Ligand binding was then evaluated by autoradiography or gamma counting.

Ligand blotting. SDS-PAGE and electro-blotting were performed as previously described. Proteins were electrophoretically separated on either 8–16% or 4–20% gradient polyacrylamide gels. After electro-blotting the proteins from the gel onto NC membranes, the blots were washed at 4° C. overnight with PBS containing 0.2% Triton X-100. The blots were then incubated in blocking buffer for 3 h at 4° C. with agitation. Ligand binding was performed by adding 10 nM $^{125}$1-AGE-BSA to the blocking buffer. After 1.5–2 h at 4° C. the blots were washed three times with blocking buffer for 1 min each and two times for 10 min each. After air drying, the ligand binding was evaluated by autoradiography.

Isolation of p60 and p90 from rat liver membranes. Unless otherwise indicated, all purification procedures were performed at 4° C. The detergent phase of the rat membrane preparation (D-phase, ~860 mg protein) was applied to a polyethylenimine cellulose column (PEI) (3×30 cm) equilibrated with TNE buffer. After washing with equilibration buffer (TNE plus 2 mM PMSF containing 1% CHAPS), the proteins bound to the PEI column were eluted by a 240 ml linear gradient of 0.1–1.5M NaCl in the equilibration buffer. Fractions were analyzed for binding activity by the solid-phase AGE binding assay. The active fractions were pooled and dialyzed overnight against TNE buffer containing 1% CHAPS. The PEI pool (160 mg protein, 80 ml) was then applied to a DEAE-cellulose column (2.5×20 cm) previously equilibrated with TNE/CHAPS/PMSF equilibration buffer. The column was washed with 4 column volumes of equilibration buffer and proteins were eluted by a 200 ml linear gradient of 0.2–1.5M NaCl in equilibration buffer. The fractions which contained AGE-BSA binding activity were pooled and concentrated by ultrafiltration (Centricon 10, Amicon). The concentrated DEAE pool (80 mg protein) was cycled three times through a BSA-Sepharose 4B column (2×12 cm, 10 mg of BSA per ml of gel), to eliminate proteins which bound to BSA. The flow-through from this BSA-Sepharose column was then applied to an AGE-BSA-Sepharose 4B column (2×6 cm, 10 mg of AGE-BSA per ml of gel) and cycled twice. The column was washed with 25 column volumes of PBS buffer, pH 7.4, containing 0.2% Triton X-100, and 1 mM PMSF. The proteins bound to the AGE-BSA column were eluted with the step-wise addition of PBS buffer containing 1.5M NaCl, 0.2% Triton X-100, and 1 mM PMSF. Each fraction was dialyzed against PBS containing 1 mM PMSF, concentrated by ultrafiltration (Centricon 30, Amicon) and analyzed for $^{125}$I-AGE-BSA binding activity by the solid-phase binding assay.

Preparative electrophoresis was performed as described in detail elsewhere. In brief, 50 μg of the protein mixture which had been affinity purified over AGE-BSA was boiled for three min in sample buffer (0.03M Tris-HCl, pH 6.8, 1% SDS, 5% glycerol, 0.015% Bromophenol Blue) in the presence of 0.1M 2-mercaptoethanol and electrophoresed through 10% polyacrylamide gels in the presence of 0.1% SDS. The 60 kD and 90 kD protein bands were excised and electro-eluted (Elutrap, Schleicher & Schuell) in Tris buffer (25 mM, pH 8.5) containing glycine (192 mM) and 0.1% SDS, as described.

Antibody generation. Laying hens were injected subcutaneously at multiple sites with a total of 100–150 Mg of electrophoretically purified p60 or p90 in complete Freund's adjuvant (Pocono Rabbit Farm and Laboratory, Canadensis, Pa.). On day 14 and 21 the hens were injected with an additional 60 μg of each protein in complete Freund's adjuvant. Further boosts of 80–100 μg of the corresponding proteins in incomplete Freund's adjuvant were given one month after the initial series. Eggs and serum from the chickens immunized with p60 or p90 proteins were separately collected. Immunoglobulins from the yolks were extracted according to the method of Polson et al., while serum immunoglobulins were isolated by a combination of ammonium sulphate (30%) precipitation and DEAE cellulose chromatography.

Western Blotting. Ten μg aliquots of detergent-solubilized samples of membrane protein were boiled in sample buffer in the presence of 0.1M 2-mercaptoethanol, and electrophoresed through gradient gels (8–16%). After transferring onto nitrocellulose, the membranes were rinsed in TBS-t buffer (10 mM Tris, 150 mM NaCl, 0.05% Tween 20) and blocked with TBS-t buffer containing 2% BSA for 1 hour at 4° C. The blots were probed with either anti-60 kD or anti-90 kD avian IgG or pre-immune chicken IgG (10 μg/ml) for 60 min at 4° C. and then washed with TBS-t buffer three times, for 5 min each. The blots were then incubated with goat anti-chicken alkaline phosphatase conjugate (1:1000 dilution) for 1 hr at 4° C. Color development was achieved according to instructions of the manufacturer (Promega, Cleveland, Ohio).

Flow Cytometric analysis

Cell preparation. Heparinized blood was drawn from male Sprague-Dawley rats (200–300 g) by cardiac puncture. Purified monocytes were prepared over Ficoll-Hypaque and Percoll gradients. Resident rat peritoneal macrophages were obtained from rats by washing the peritoneal cavity with 20 ml of PBS and were characterized by flow cytometry.

Fluorescence Flow Cytometry. The expression of p60 and p90 AGE-binding proteins on rat monocytes and macrophages was determined by indirect immunofluorescence. Single color cell staining was performed by incubating one million cells with biotinylated anti-p60 or anti-p90 primary antibodies at a final concentration of 5 μg/ml for 20 min at 4° C. Cells were washed in staining buffer (PBS, 3% FBS, 0.1% NaN$_3$) and then incubated with FITC-conjugated avidin (Becton Dickinson, Mountain View, Calif.). Background fluorescence was determined by staining the cells with a relevant isotypic control antibody, biotinylated chicken IgG used in identical concentrations (5 µg/ml). Cells were analyzed using a FACSCAN (Becton Dickinson, Mountain View, Calif.) with gates set by forward angle light scatter and side scatter. Fluorescence emission for FITC was detected by selectively collecting at 500–537 nm on at least 5000 labeled cells, gated to include monocytes/macrophages and to exclude lymphocytes, other non-monocytic cells and dead cells. The data were analyzed by Paint-A-Gate software (Consort 30, Becton Dickinson, Mountain View, Calif.).

For the cross-competition study, $10^6$ rat monocytes were treated with either 5 µg/ml biotinylated anti-p60 antibodies in the presence of 20-fold excess anti-p90 antibodies, or 5 µg/20 µl biotinylated anti-p90 in the presence of 20-fold excess anti-p60. The antibody-treated cells were then labeled using FITC-avidin and analyzed by flow cytometry.

RESULTS

Figure 5B:
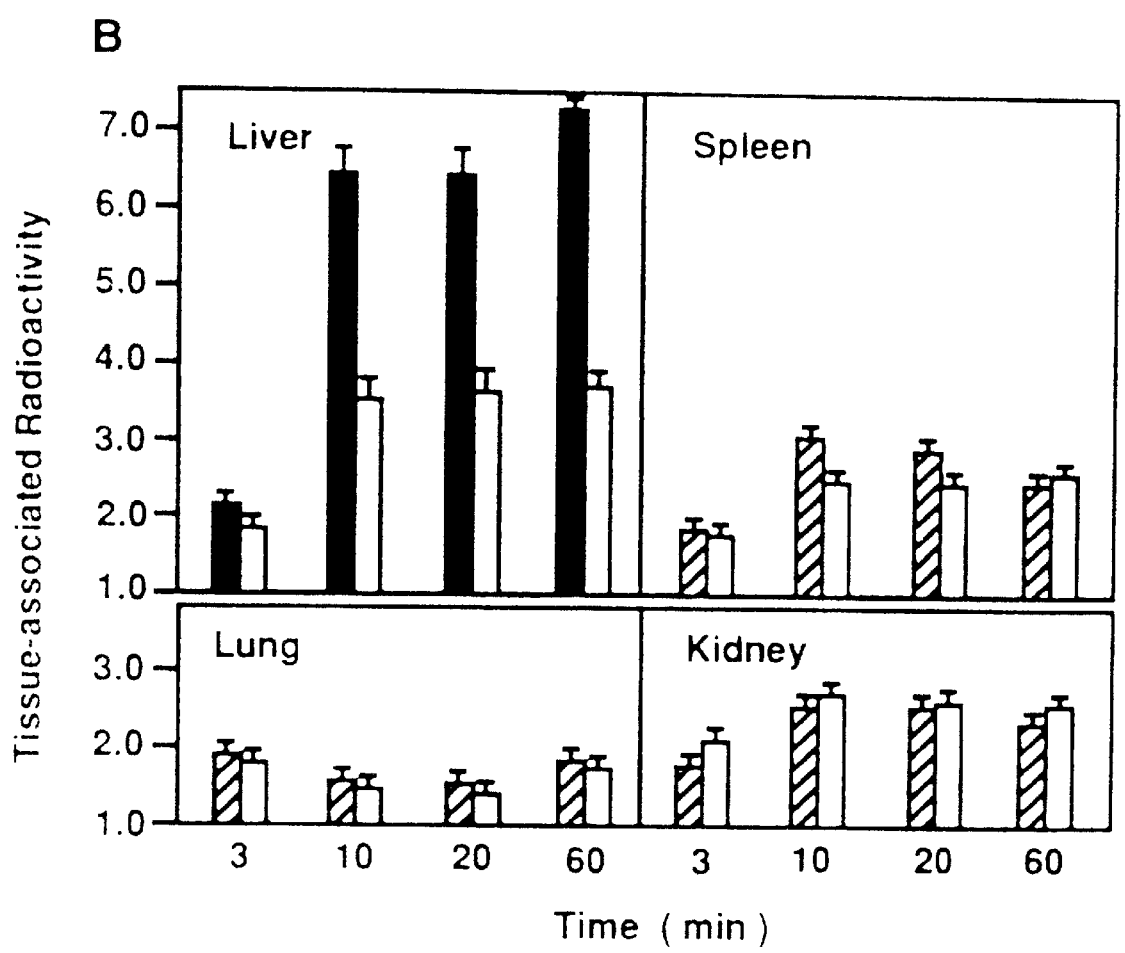
FIG. 5(B)—Specific competition of $^{125}$I-AGE-RSA uptake in rat liver, spleen, lung and kidney. Immediately prior to receiving radio-labeled ligand, rats were injected with excess non-labeled AGE-RSA (5 mg, i.v.). At the indicated time intervals, incorporated radioactivity was determined in blood and tissues, and compared according to a Tissue-to-Blood Isotope Ratio (TBIR) formula as described in text. Closed and striped bars: $^{125}$I-AGE-RSA (50 µg) alone. Open bars: $^{125}$I-AGE-RSA (50 µg) in the presence of excess non-labeled AGE-RSA. Data are expressed as mean±SEM of three independent measurements performed in five animals per group.

In vivo tissue distribution of AGE-binding activity. Applicants previously identified a 90 kD protein on mouse and human monocytes/macrophages which selectively binds AGE-proteins. Since these sources are not convenient to provide sufficient material for further biochemical characterization, alternate tissue sources were sought. As a first step, the distribution of AGE-specific binding activity in rat tissues was examined by uptake studies of $^{125}$I-AGE-RSA. Either $^{125}$I-AGE-RSA (50 µg, $8.3\times10^5$ cpm/µg) or $^{125}$I-normal RSA (50 µg, $6.2\times10^5$ cpm/µg) was injected intravenously into rats along with $^{51}$Cr-labeled RBC, as described in Methods. After 10 minutes, greater than 50% of the AGE-RSA was concentrated in the liver, whereas the liver uptake of non-modified $^{125}$I-RSA was consistently less than 10% of the AGE-RSA values (FIG. 5A). Tissue accumulation of AGE-RSA was not affected by the prior injection of 100-fold excess non-labeled RSA (5 mg, not shown). In contrast, pre-treatment of rats with excess non-labeled AGE-RSA (5 mg) decreased the accumulation of AGE-BSA in the liver by about 45% after 10, 20 and 60 minute intervals (FIG. 5B). The uptake of AGE-RSA remained uniformly low in all other major organs, with or without the non-labeled competitor. It was apparent that the liver had a high specific capacity to accumulate AGE-protein and therefore represented a potentially rich source for the isolation of the AGE-binding proteins.

1. AGE-binding assay

Figure 6A:
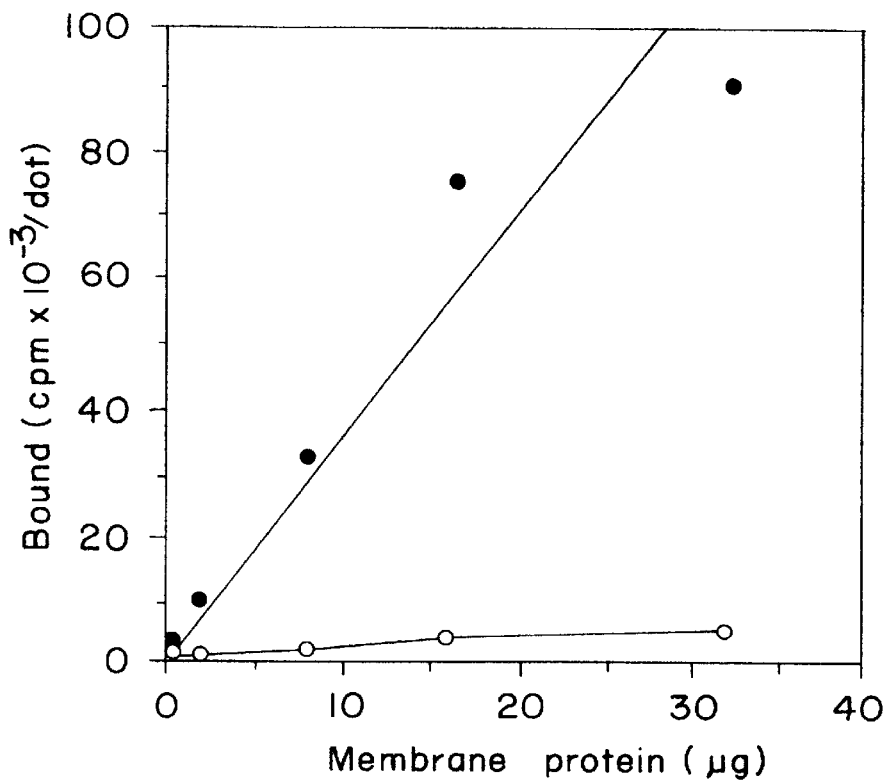
FIG. 6(A): Relationship of liver membrane protein concentration to AGE-ligand binding. Aliquots (1–50 µg) of a detergent-solubilized liver membrane protein preparation were immobilized on nitrocellulose filters, incubated with blocking buffer, and then probed for AGE-protein binding activity with $^{125}$I-AGE-BSA in the presence or absence of excess non-labeled AGE-BSA. After washing, the blots were counted for $^{125}$I. Closed circles: $^{125}$I-AGE-BSA alone (total binding). Open circles: $^{125}$I-AGE-BSA plus 100-fold excess non-labeled AGE-BSA (non-specific binding). Data points represent duplicate blots.
Figure 6B:
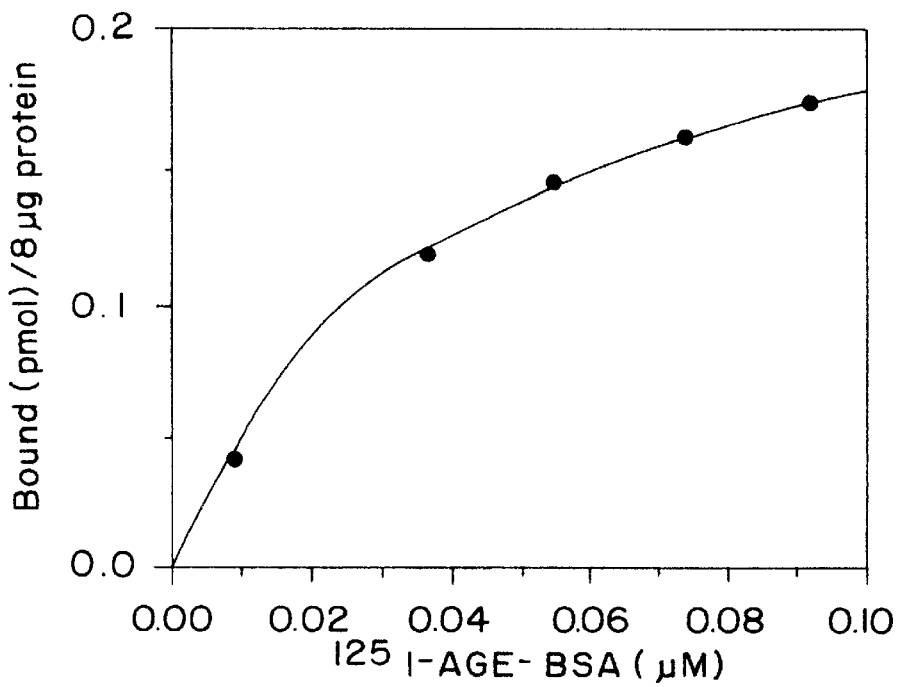
FIG. 6(B) Saturability of $^{125}$I-AGE-BSA binding. A fixed amount of solubilized liver membrane proteins (8 µg) was immobilized on duplicate nitrocellulose filters which were probed with increasing concentrations of $^{125}$I-AGE-BSA (10–100 nM, s.a.=1.5×10$^5$ cpm/ng) in the presence (non-specific) or absence (total binding) of 200-fold excess non-labeled AGE-BSA. After washing, the nitrocellulose filters were counted for retained $^{125}$I. Specific binding was determined by subtracting non-specific binding from total binding.
Figure 6C:
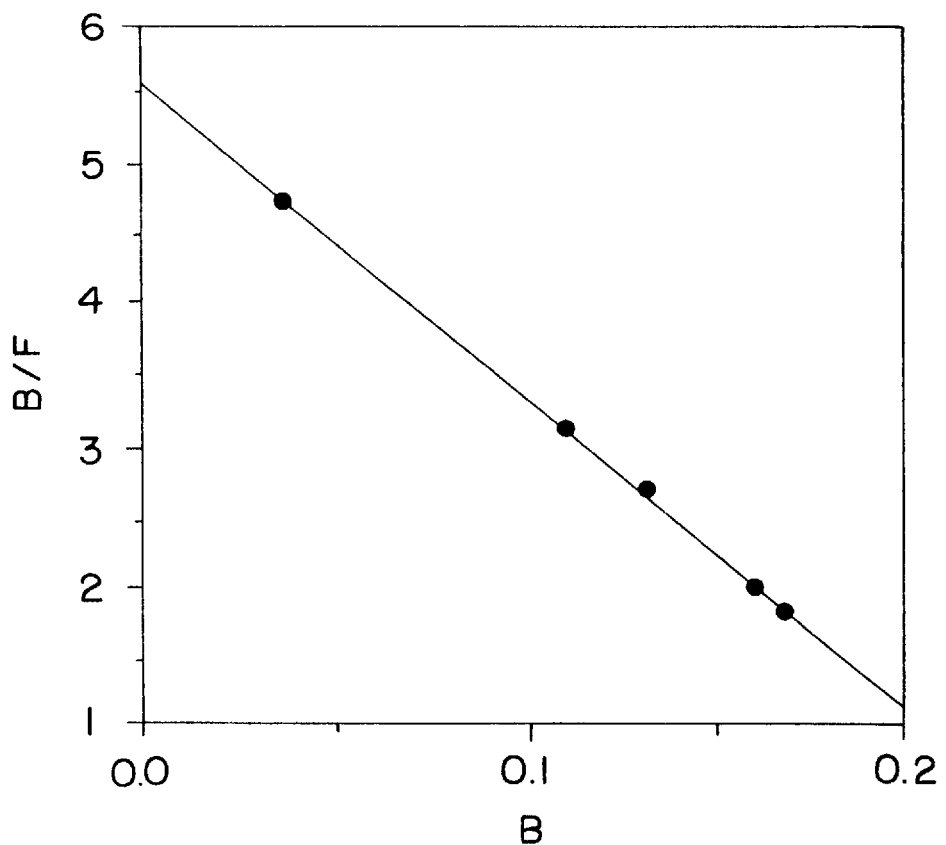
FIG. 6(C): Scatchard analysis of specific binding data (B=pmoles/8 µg membrane protein, F=µM).

To facilitate the isolation of the AGE-binding proteins from liver a solid-phase assay system was developed involving the immobilization of detergent-solubilized membrane proteins onto nitrocellulose and probing for ligand-specific binding activity with $^{125}$I-AGE-BSA as described in Methods. FIG. 6A shows the effect of increasing amounts of crude liver membrane proteins on AGE-ligand binding. Total AGE-BSA binding increases in proportion to the amount of membrane proteins immobilized on the filters, whereas non-specific binding was negligible. The AGE-binding kinetics of these membrane proteins after blotting onto nitrocellulose is shown in FIG. 6B. When ~8 µg of hepatic membrane proteins immobilized onto NC filters were incubated with increasing amounts of $^{125}$I-AGE-BSA, saturable binding was observed with a $B_{max}$ of 0.22 pmol/8 µg of protein (FIG. 6C). A dissociation constant ($K_d$ of $4\times10^{-8}$M) was revealed by Scatchard analysis of the binding data.

Figure 6D:
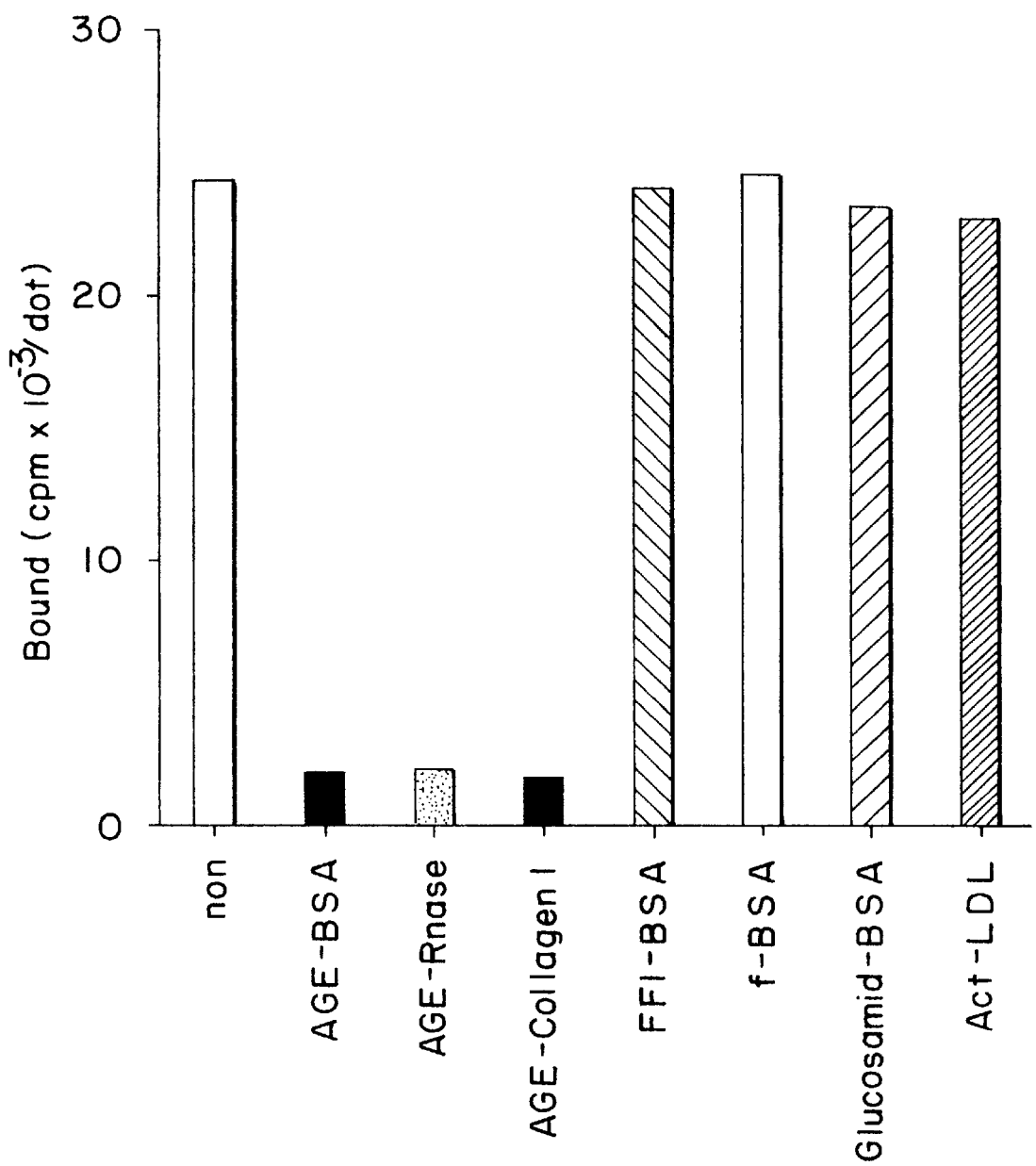
FIG. 6(D): Effects of differently modified protein ligands on $^{125}$I-AGE-BSA binding. Filter blots of solubilized liver membranes prepared as above were probed with $^{125}$I-AGE-BSA (50 nM) alone, or in the presence of 150-fold excess of various non-labeled competitors: AGE-albumin (AGE-BSA), AGE-ribonuclease (AGE-RNAse), AGE-collagen I, FFI-BSA, formaldehyde-treated albumin (f-alb), glucosamide BSA, acetyl-LDL (act-LDL). Data are expressed as the amount of $^{125}$I-AGE-BSA (cpm×10$^{-3}$) retained on duplicate blots.

The specificity of liver cell binding activity for AGE adducts on protein was determined in competition experiments testing $^{125}$I-AGE-BSA against several different AGE-protein competitors, as well as against ligands known to bind to other scavenger receptors (FIG. 6D). The addition of 150-fold excess AGE-RNAse or AGE-collagen I completely inhibited the binding of radio-labeled AGE-BSA to crude hepatic membrane protein extracts immobilized on NC filters. In contrast FFI-BSA, formaldehyde-treated BSA, glucosamide-BSA (a chemically linked glucose-BSA compound) or acetyl-LDL did not compete against the binding of labeled AGE-BSA.

Using similar detergent-solubilized membrane preparations from heart, kidney, brain, or lung obtained by identical procedures as described for liver, $^{125}$I-AGE-BSA specific binding activity was examined by the same solid-phase AGE-binding assay. Liver membrane proteins exhibited the highest binding activity among all tissues examined, consistent with our in vivo observations (data not shown).

2. Purification of rat liver AGE-binding proteins

Using the solid-phase AGE binding assay as a means of monitoring AGE-binding activity column fractions, the isolation of AGE-binding protein(s) was pursued by the procedure outlined in Table 1 and described in detail in Materials and Methods. In brief, rat liver membrane proteins were solubilized in Triton X-114. After detergent phase-separation, the D-phase was subjected to chromatography on PEI-cellulose, DEAE-cellulose, BSA-Sepharose, and finally, AGE-BSA-Sepharose. After elution from the AGE-BSA Sepharose column, the fractions were assessed for AGE-binding activity by the solid-phase AGE binding method (FIG. 7).

Figure 7:
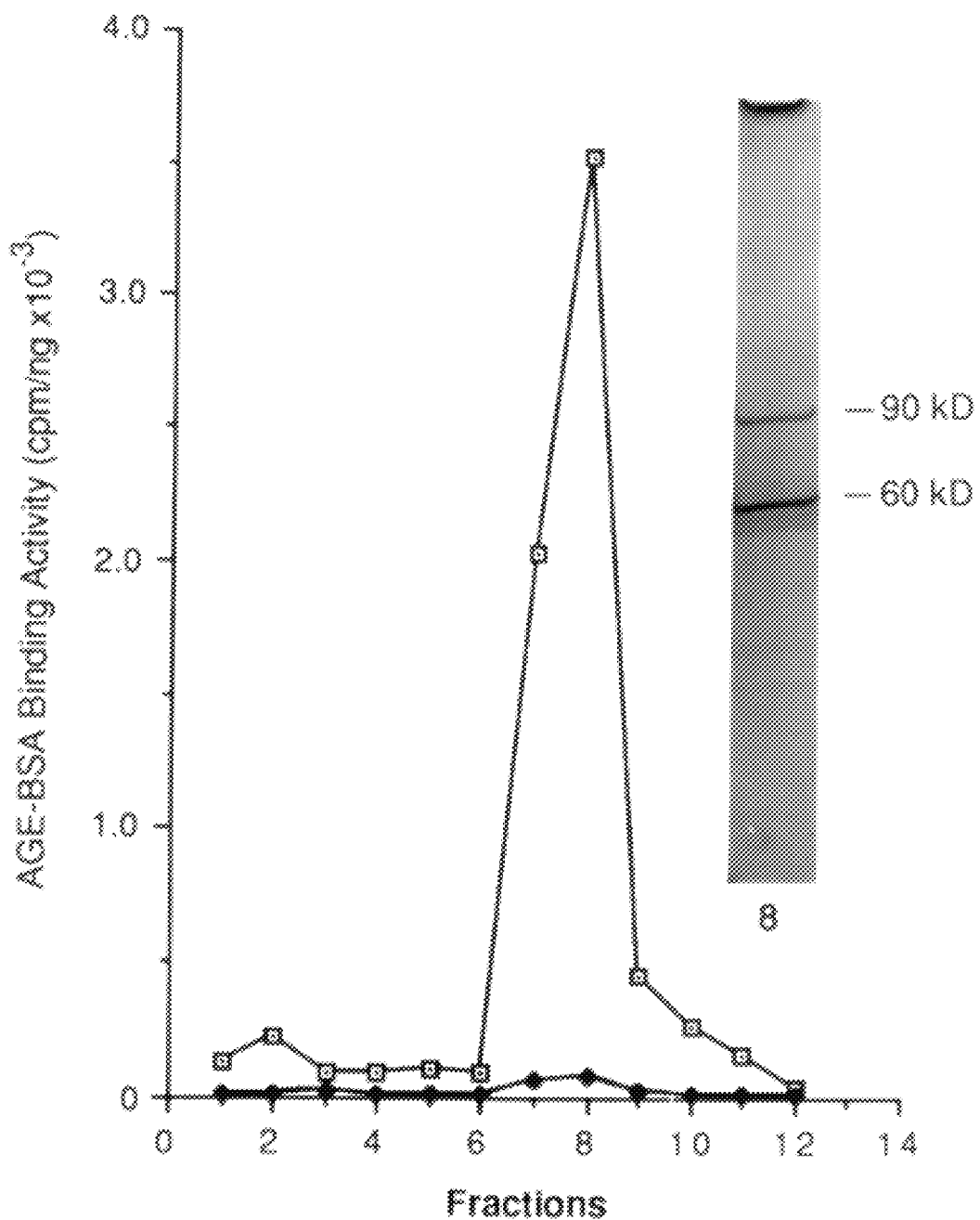
FIG. 7 shows the purification of rat liver AGE-binding proteins. Detergent-solubilized membrane proteins were fractionated by successive PEI-cellulose, DEAE-cellulose, and BSA-Sepharose 4B column chromatography, as described in Methods. The flow-through from the BSA-Sepharose column was then applied to an AGE-BSA-Sepharose 4B column. This column was washed and bound proteins were eluted by the addition of high salt buffer. Each fraction was concentrated and analyzed for AGE-binding activity using the binding assay described in FIG. 6. Open circles: total binding activity; closed circles: non-specific activity. Inset: SDS-PAGE analysis of fraction #8 (mercaptoethanol reduced), and stained with Coommassie Blue.

Analytical SDS-PAGE electrophoresis of the active fractions obtained from the AGE-BSA-column revealed the presence of two main protein bands with approximate molecular weights of 60 kD (p60) and 90 kD (p90) (FIG. 7, inset). In order to separate larger amounts of these AGE-binding proteins, AGE-BSA column eluate fractions were subjected to preparative PAGE and the individual proteins were separately electro-eluted from respective gel slices.

Gel-purified p60 and p90 were blotted onto Immobilon membranes and amino terminal sequences were obtained at the Rockefeller University sequencing facility. Table 7 records the N-terminal sequence obtained from each of these proteins, which data is also presented herein in FIGS. 11 and 12. Comparison of these sequences with the translated Genbank database did not reveal significant similarity to other known proteins.

Ligand blotting of p60 and p90 proteins immobilized on nitrocellulose, using $^{125}$I-AGE-BSA as probe, revealed that only the 60 kD protein bound this ligand (not shown). After blotting on nitrocellulose, the 90 kD protein did not bind $^{125}$I-AGE-BSA, although p90 did bind to the AGE-BSA-Sepharose matrix and was not retained on the BSA-Sepharose column.

When crude rat liver membrane proteins (D-phase) were separated by SDS-PAGE under non-reducing conditions, transferred to NC filters, and probed for ligand binding with $^{125}$I-AGE-BSA, a single major AGE-BSA binding band at an approximate molecular mass of 60 kD was revealed (FIG. 8A, lane 1). The binding of this protein to AGE-BSA was inhibited partially in the presence of a 25-fold excess (lane 2) and completely by a 150-fold excess of non-radioactive AGE-BSA (lane 3). No other prominent bands were observed under these conditions. It thus appears likely that nitrocellulose immobilization may inactivate the binding properties of p90, or that p90 is a p60-associated protein which lacks independent AGE-binding activity.

3. Immuno-characterization of AGE-binding proteins

Figure 8B:
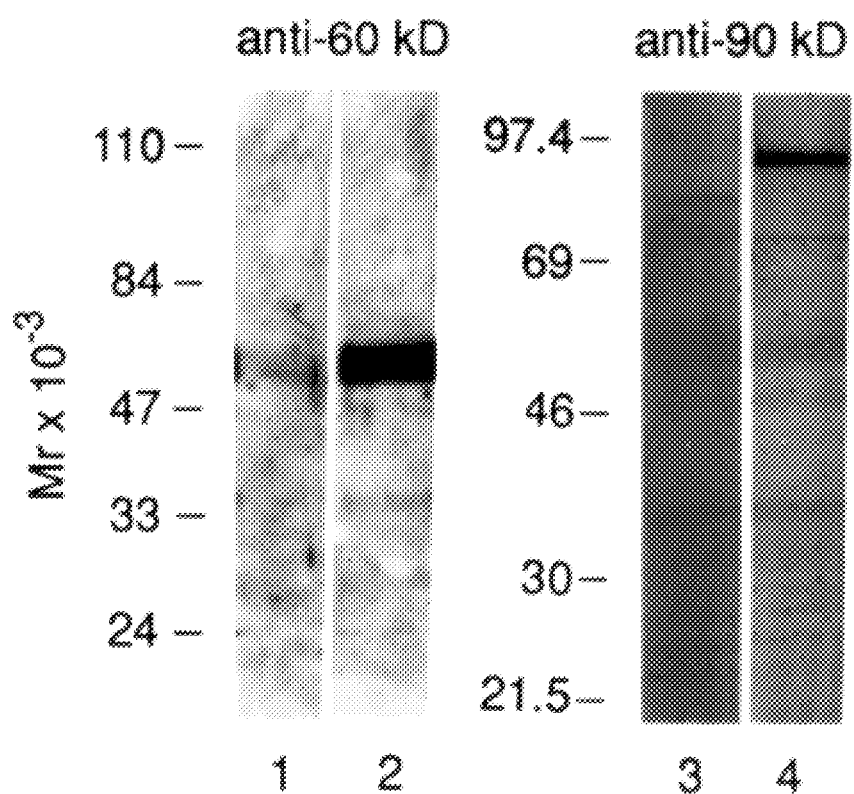
FIG. 8(B) Aliquots of solubilized membrane proteins (mercaptoethanol reduced), were electrophoresed through an 8–16% gradient gel and electro-transferred onto nitrocellulose filters. After washing and blocking with excess BSA, the blots were probed with purified IgG fractions of either anti-p60 or anti-p90 chicken antisera or the corresponding preimmune sera, and then exposed to goat anti-chicken antibody conjugated to alkaline phosphatase and reacted for phosphatase-dependent color development. Lane 1, preimmune IgG; Lane 2, anti-p60 IgG; Lane 3, preimmune IgG, Lane 4, anti-p90 IgG. Results are representative of three independent experiments.

Purified p60 and p90 proteins were injected into chickens in order to obtain specific polyclonal antibodies. Preparation of avian IgG specific for each of the proteins were isolated either from egg yolk or serum as described in Materials and Methods. The specificity of each of the antibodies was verified by Western blot analysis, using the same crude liver membrane protein extract analyzed above by ligand blotting (FIG. 8B). The antibody to the p60 AGE-binding protein recognized a major protein band at approximately 60 kD (lane 2), while the pre-immune IgG did not (lane 1). Similarly the antibody to p90 recognized a single protein band at about 90 kD (lane 4), whereas the pre-immune antibodies did not (lane 3).

Figure 9:
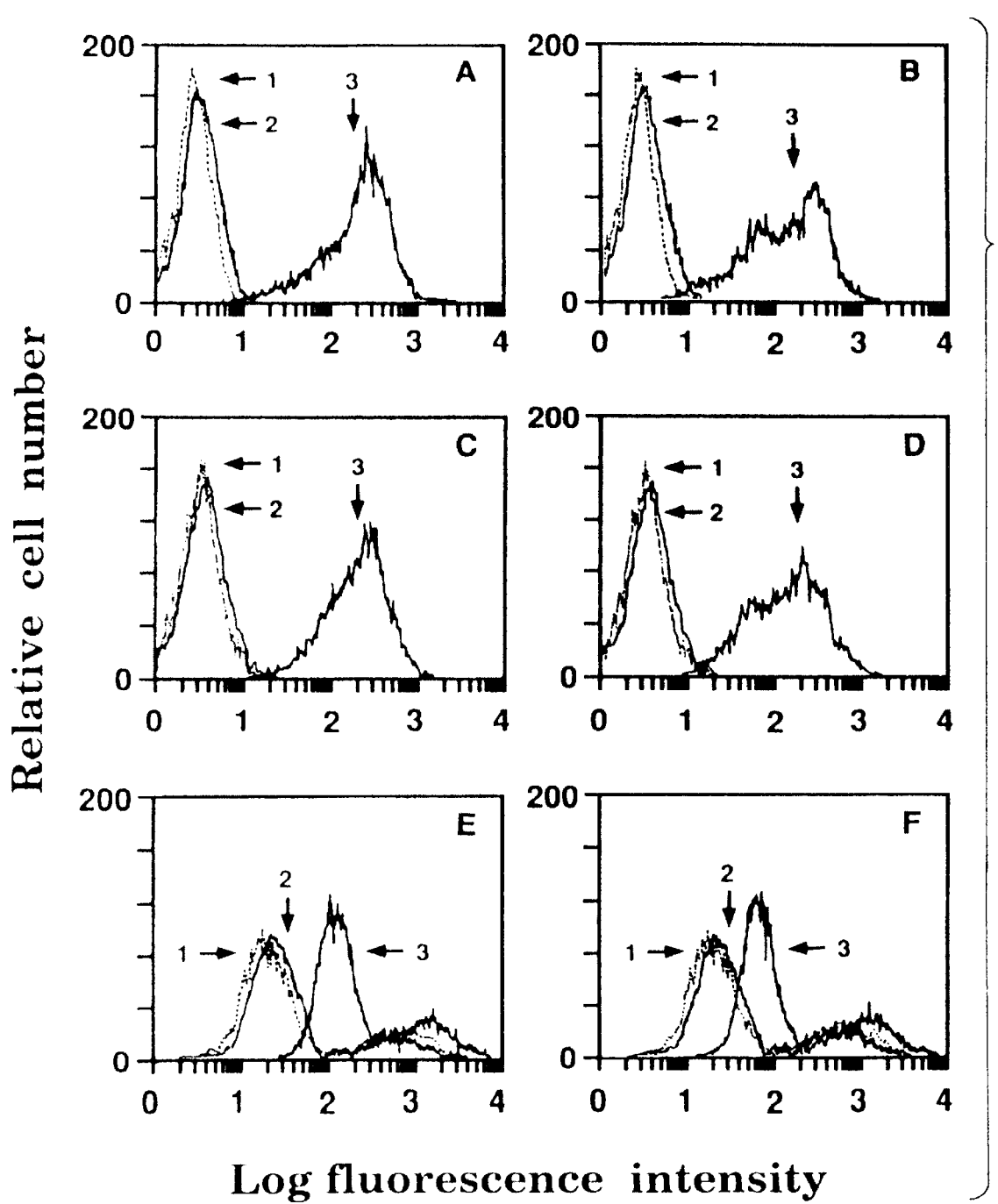
FIG. 9—Demonstration by flow cytometry of expression of p60 and p90 AGE-binding proteins rat monocytes and macrophages. Peripheral blood monocytes (A–D) and peritoneal resident macrophages (E and F) were treated with biotinylated anti-p60 alone (A and E), biotinylated anti-p90 alone (B and F), biotinylated anti-p60+20-fold excess unconjugated anti-p90 (C), biotinylated anti-p90+20-fold excess unconjugated anti-p60 (D), followed by FITC-avidin and analyzed by FACSCAN. Arrow 1: Fluorescence of cells treated with FITC-avidin in the absence of either anti-p60 or anti-p90 (dotted line). Arrow 2: Fluorescence of cells treated with FITC-avidin subsequent to treatment with biotinylated chicken IgG (isotypic control). Arrow 3: Fluorescence of cells treated with FITC-avidin subsequent to treatment of cells with biotinylated anti-p60 (A,C,E) and anti-p90 (B,D, F). Note the lack of competition between a 20-fold excess of unconjugated anti-p90 for the binding of anti-p60 to the monocytes (panel A vs C), and the lack of competition between a 20-fold excess of unconjugated anti-p60 for the binding of anti-p90 to the monocyte cell surface (panel B vs D). All antibodies were used at a final concentration of 5 μg/ml, unless otherwise indicated.

The antibodies to p60 and p90 were used to screen for the expression of these proteins on the surface of rat peripheral blood monocytes and peritoneal macrophages. FACS analyses which demonstrated the presence of each protein on the surface of both cell types are shown in FIG. 9. Panels A and B illustrate flow cytometric detection of p60 and p90 on the surface of rat monocytes. FIG. 9 also shows that the binding of either anti-p60 or anti-p90 to the monocyte cell surface was not affected by a 20-fold excess of the heterologously directed antibody (panels C and D respectively). Distinct binding of the anti-p60 and anti-p90 antibodies was also observed when the rat peritoneal resident macrophages were analyzed by flow cytometry (FIG. 9, panels E and F, respectively). A small subgroup of highly fluorescent cells of an unspecified nature with a non-specific FITC staining pattern was also noted, using antibody as well as isotypic controls.

Figure 10A:
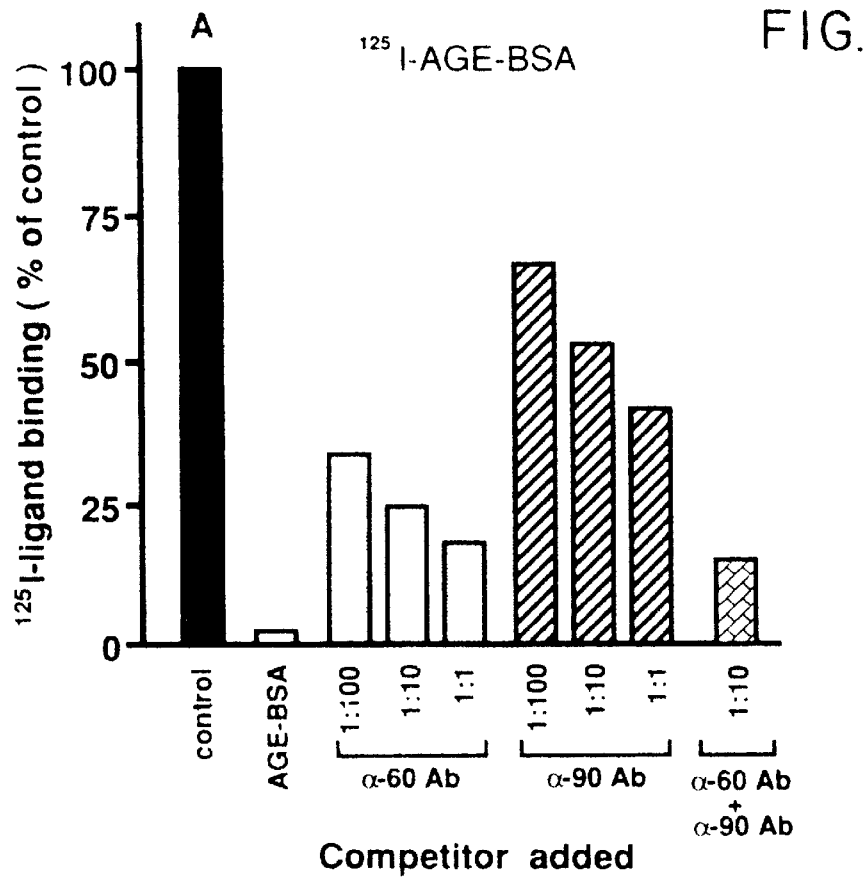
FIG. 10—Inhibition of $^{125}$I-AGE-BSA binding (FIG. 10A) and $^{125}$I-FFI-BSA binding (FIG. 10B) on rat macrophage cell surface by anti-p60 and anti-p90 antibodies. Rat peritoneal resident macrophages were collected by peritoneal lavage and purified, then incubated with the indicated radio-labeled ligand in the presence or absence of a 10-fold excess of non-labeled ligand or in the presence of antibodies p60 or p90-specific at the indicated dilutions. Both antibodies were used alone (undiluted: 2 μg/200 μl) or in combination (at 1:10 dilution). Data are expressed as % of maximal control binding (defined as the amount of $^{125}$I-ligand bound to the cell surface in the presence of 10% FBS) and represent the mean of duplicate experiments.
Figure 10B:
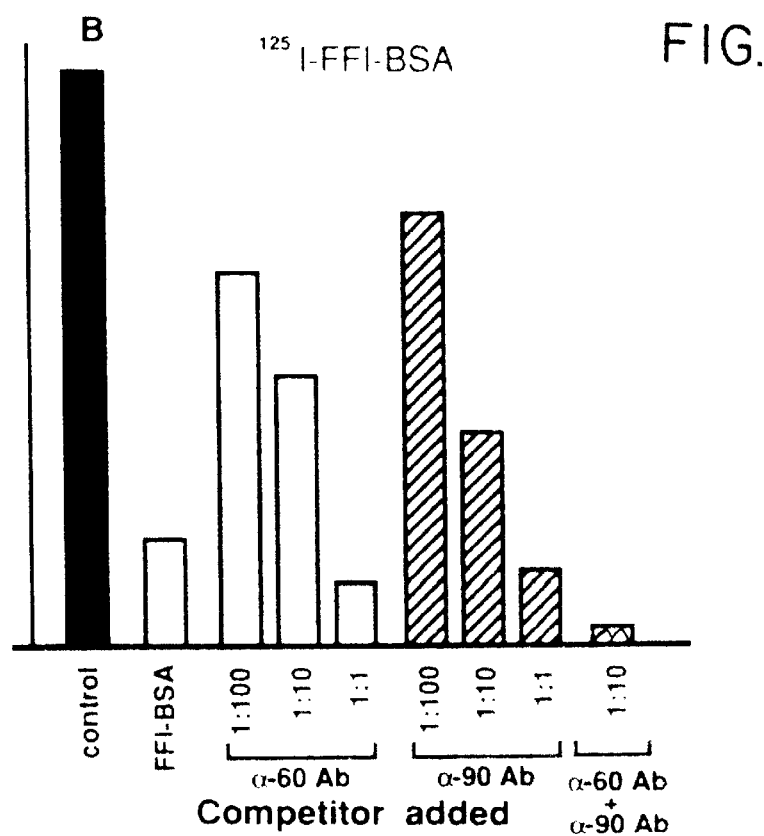

In order to confirm that p60 and p90 were both AGE-binding proteins expressed independently on rat peritoneal resident macrophages, $^{125}$I-AGE-BSA binding inhibition experiments were carried out using each antibody separately (undiluted: 10 μg/ml) as well as in combination (FIG. 10A). In the presence of increasing concentrations of anti-p60 antibody significant AGE-BSA binding inhibition was observed (up to 80% at a final concentration of 10 μg/ml). Similarly $^{125}$I-AGE-BSA binding was inhibited up to 60% by the anti-p90 antibody, while the combination of both antibodies at a dilution of 1:10 provided 84% inhibition. When radio-labeled FFI-BSA (made from the chemically synthesized model AGE compound, FFI, crosslinked onto BSA with a carbodiimide reagent) was used as the ligand, anti-p60 as well as anti-p90 mediated a concentration-dependent inhibition of FFI-modified BSA binding (FIG. 10B). Moreover, and as found with AGE-BSA, a combination of anti-p60 and anti-p90 antibodies exerted greater inhibition compared to either anti-p60 alone or anti-p90 alone. No inhibitory effect was noted when isotypic control antibodies were used, even at the maximal concentration, in conjunction with either modified BSA ligand (not shown).

TABLE I

Purification of Rat Liver AGE Binding Proteins $^{125}$I-AGE-BSA Binding

| Purification Step | Total Protein (mg) | Total μg | Specific Activity (μg/mg) | Purification factor | Recovery (%) |
|---|---|---|---|---|---|
| Liver Membrane | 6,800 | 455.5 | 0.067 | 1 | 100 |
| D-phase | 830 | 207.5 | 0.256 | 3.7 | 45 |
| PEI | 175 | 262.2 | 1.498 | 22 | 58 |
| DEAE | 82 | 153.5 | 7.490 | 109 | 34 |
| AGE-affinity | 0.560 | 92.4 | 165 | 2463 | 20 |
| Preparative PAGE* | 0.180 | — | — | — | — |

Rat liver membrane proteins were procured and prepared as described. Specific binding of AGE-BSA was determined by the solid phase binding assay.
*Binding activity could not be determined due to the presence of SDS.

TABLE II

N-Terminal Amino Acid Sequence Analysis of AGE-Binding Proteins from Rat Liver

| 60 kD: | XGPRTLVLLDNLNVRDTHXLFF |
| 90 kD: | XEVKLPDMVSLXD |

X INDICATES UNIDENTIFIED RESIDUES.

DISCUSSION

The above experiments confirm the isolation and discovery of two novel rat liver membrane proteins, designated p60 and p90 by their migration SDS-PAGE, which specifically bind to protein ligands modified by advanced glycosylation endproducts (AGEs). Amino terminal sequence analysis indicates that these proteins bear no significant homology to each other nor to any previously sequenced proteins currently available in the Genbank database. Both p60 and p90 are present on rat monocytes and macrophages and are immunoreactively and functionally distinct. Of importance is the fact that these binding proteins have been distinguished from both the recently reported macrophage scavenger receptor for acetyl-LDL, a functional trimer composed of three 77 kD glycoprotein subunits; and from the binding proteins for formaldehyde-treated albumin with $M_r$'s of 30 and 52 kD.

The p60 and p90 AGE-binding proteins were isolated from rat liver, upon the determination that this organ acts as a major filter for the in vivo clearance of AGE-modified macromolecules; liver presents the highest capacity to specifically sequester AGE-proteins administered intravenously (FIG. 5). An isolation procedure, including elution of detergent-solubilized membrane proteins from an AGE-protein affinity matrix was devised, and the p60 and p90 AGE-binding proteins were found to co-purify. When immobilized on nitrocellulose, however, only p60 retained binding activity for AGE-modified ligands. Just as they co-purify over anion exchange and ligand affinity columns, p60 and p90 were also observed to co-purify in hydroxylapatite chromatography (not shown). The extent of this co-purification continues to be examined.

The liver is a complex organ containing several cell types, including macrophages and endothelial cells, both of which have been shown to bear AGE-receptors. To determine whether macrophages also expressed a 60 kD AGE-binding protein, and whether there was any relationship between the macrophage 90 kD and the liver p90 AGE-binding proteins, specific polyclonal antibodies to liver p60 and p90 were developed.

The specificity of these antibodies was demonstrated by Western analysis of crude liver membrane extracts, revealing that each antiserum identified a single protein band of the appropriate molecular weight. Flow cytometric analysis of rat peripheral monocytes and peritoneal resident macrophages revealed that each antisera bound to the surface of both of these cell types. Cross-competition studies performed on monocytes revealed no cross-reactivity between the two antibodies. These data indicate that the p60 and p90 AGE-binding molecules originally isolated from whole liver preparations are each present on monocytes as well as macrophages (FIG. 9).

Flow cytometric binding inhibition experiments clearly demonstrated that p60 and p90, expressed on the surface of monocytes/macrophages, independently bound AGE-modified ligands. Interestingly, a combination of antibodies specific for p60 and p90 mediated greater inhibition of AGE-protein binding than did either antibody alone.

Either antiserum, used independently or in combination, prevented more than 90% of binding FFI-BSA to rat macrophages. In the case of p60, this finding is surprising given that this binding protein does not bind FFI-BSA in a solid-phase ligand blotting assay. With regard to liver p90, the flow cytometry and FFI-binding inhibitory data indicate that this molecule may be closely related to the 90 kD protein isolated from murine RAW 264.7 cells. In fact, preliminary experiments using antibodies raised against rat liver p60 and p90 proteins to stain mouse RAW cells provided flow cytometric and binding inhibition results similar to those obtained with rat monocytes and macrophages, strongly supporting a structural similarity between the AGE-binding proteins of these two rodent species.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. An isolated antibody that binds a receptor protein, said receptor protein to which said antibody is raised comprising a protein in purified form derived from rat liver cell membranes, that recognizes and binds advanced glycosylation endproducts (AGE) and that possesses the following characteristics:

A. said protein recognizes and binds with the ligands AGE-RNase and AGE-Collagen I;

B. said protein does not recognize and bind with the ligands FFI-BSA, formaldehyde-treated BSA, glucosamide-BSA, and acetyl LDL-BSA in solid phase ligand blotting assay; and C. said protein has a molecular mass of about 90 kD or about 60 kD as determined by protein migration on SDS-PAGE.

2. The antibody of claim 1 wherein said protein has the following characteristics:

A. said protein is found on rat liver cell membranes;

B. said protein is expressed on rat monocytes and rat macrophages; and

C. said protein is purified by elutions based, respectively, on an AGE ligand affinity column, and anion exchange column, and a hydroxylapatite column;

and also bears the following distinction:

D. when said protein has a molecular mass of about 90 kD, as determined by SDS Page, and it is immobilized on nitrocellulose in a solid phase assay, the 90 kD protein does not bind to AGE-modified ligands, and when the protein has a molecular mass of about 60 kD, as determined by SDS Page, said protein binds to AGE modified ligands when immobilized on nitrocellulose in a solid phase assay.

3. The antibody of claim 1 wherein said receptor is isolated and purified by the immobilization of detergent-solubilized rat liver membrane proteins on nitrocellulose in accordance with a solid phase assay protocol.

4. The antibody of claim 1 wherein the said protein as determined by SDS Pages has a molecular mass of about 90 kD, and the $NH_2$-terminal partial amino acid sequence set forth in FIG. 11 (SEQ ID NO.2).

5. The antibody of claim 1 whrein the said protein as determined by SDS Page has a molecular mass of about 60 kD and the $NH_2$-terminal partial amino acid sequence set forth in FIG. 12 (SEQ ID NO.1).

6. The antibody of claim 1 which is a polyclonal antibody.

7. The antibody of claim 1 which is a monoclonal antibody.

8. An immortal cell line that produces a monoclonal antibody according to claim 7.

9. The antibody of claim 1 labeled with a detectable label.

10. The antibody of claim 9 wherein the label is selected from the group consisting of enzymes, chemicals which fluoresce and radioactive elements.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rat
        ( G ) CELL TYPE: Liver membrane ( i x ) FEATURE:
        ( A ) NAME/KEY: Region
        ( B ) LOCATION: 1..13
        ( C ) OTHER INFORMATION: Xaa denotes unidentified residues ( x i ) SEQUENCE DESCRIPTION: SEQ ID NO:1:

Xaa  Glu  Val  Lys  Leu  Pro  Asp  Met  Val  Ser  Leu  Xaa  Asp
    1                   5                       10

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide -continued

```
( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rat
        ( B ) CELL TYPE: Liver Membrane ( i x ) FEATURE:
        ( A ) NAME/KEY: Region
        ( B ) LOCATION: 1..23
        ( C ) OTHER INFORMATION: Xaa denotes unidentified residues ( x i ) SEQUENCE DESCRIPTION: SEQ ID NO:2:

Xaa  Gly  Pro  Arg  Thr  Leu  Val  Leu  Leu  Asp  Asn  Leu  Asn  Val  Arg
 1                  5                        10                       15

Arg  Asp  Thr  His  Xaa  Leu  Phe  Phe
                    20
```